US010512936B2

(12) United States Patent
Alie et al.

(10) Patent No.: US 10,512,936 B2
(45) Date of Patent: Dec. 24, 2019

(54) MICROFABRICATED ULTRASONIC TRANSDUCER HAVING INDIVIDUAL CELLS WITH ELECTRICALLY ISOLATED ELECTRODE SECTIONS

(71) Applicant: Butterfly Network, Inc., Guilford, CT (US)

(72) Inventors: Susan A. Alie, Stoneham, MA (US); Keith G. Fife, Palo Alto, CA (US); Joseph Lutsky, Los Altos, CA (US); David Grosjean, Holliston, MA (US)

(73) Assignee: Butterfly Network, Inc., Guilford, CT (US)

( * ) Notice: Subject to any disclaimer, the term of this patent is extended or adjusted under 35 U.S.C. 154(b) by 0 days.

(21) Appl. No.: 16/012,999

(22) Filed: Jun. 20, 2018

(65) Prior Publication Data

US 2018/0369862 A1    Dec. 27, 2018

Related U.S. Application Data

(60) Provisional application No. 62/522,875, filed on Jun. 21, 2017.

(51) Int. Cl.
*B06B 1/02* (2006.01)
*B81C 1/00* (2006.01)
(Continued)

(52) U.S. Cl.
CPC .......... *B06B 1/0292* (2013.01); *B81B 3/0021* (2013.01); *B81B 3/0078* (2013.01);
(Continued)

(58) Field of Classification Search
CPC ... B06B 1/0292; B81B 3/0021; B81B 3/0078; B81C 1/00238; B81C 1/00246
See application file for complete search history.

(56) References Cited

U.S. PATENT DOCUMENTS 5,286,671 A    2/1994   Kurtz et al.
6,430,109 B1   8/2002   Khuri-Yakub et al.
(Continued)

FOREIGN PATENT DOCUMENTS

CN    101558552 A    10/2009
CN    101573861 A    11/2009
(Continued)

OTHER PUBLICATIONS

International Search Report and Written Opinion dated Sep. 18, 2018 in connection with International Application No. PCT/US2018/038429.
(Continued)

*Primary Examiner* — Nathan W Ha
(74) *Attorney, Agent, or Firm* — Wolf, Greenfield & Sacks, P.C.

(57) ABSTRACT

An ultrasonic transducer includes a membrane, a bottom electrode, and a plurality of cavities disposed between the membrane and the bottom electrode, each of the plurality of cavities corresponding to an individual transducer cell. Portions of the bottom electrode corresponding to each individual transducer cell are electrically isolated from one another. Each portion of the bottom electrode corresponds to each individual transducer that cell further includes a first bottom electrode portion and a second bottom electrode portion, the first and second bottom electrode portions electrically isolated from one another.

6 Claims, 14 Drawing Sheets

(51) Int. Cl.
*G01N 29/24* (2006.01)
*B81B 3/00* (2006.01)
*G01N 29/22* (2006.01)

(52) U.S. Cl.
CPC ...... *B81C 1/00238* (2013.01); *B81C 1/00246* (2013.01); *G01N 29/226* (2013.01); *G01N 29/2406* (2013.01); *B81B 2201/0271* (2013.01); *B81B 2203/0127* (2013.01); *B81B 2203/0315* (2013.01); *B81B 2203/04* (2013.01); *B81B 2207/015* (2013.01); *B81C 2203/035* (2013.01); *B81C 2203/036* (2013.01); *B81C 2203/0728* (2013.01); *B81C 2203/0792* (2013.01); *G01N 2291/106* (2013.01)

(56) References Cited

U.S. PATENT DOCUMENTS

| | | | |
|---|---|---|---|
| 6,443,901 B1 | 9/2002 | Fraser | |
| 6,610,582 B1 | 8/2003 | Stewart | |
| 6,645,145 B1 | 11/2003 | Dreschel et al. | |
| 6,659,954 B2 | 12/2003 | Robinson | |
| 6,694,817 B2 | 2/2004 | Degertekin et al. | |
| 6,779,387 B2 | 8/2004 | Degertekin | |
| 6,795,374 B2 | 9/2004 | Barnes et al. | |
| 6,831,394 B2 | 12/2004 | Baumgartner et al. | |
| 6,865,140 B2 | 3/2005 | Thomenius et al. | |
| 6,958,255 B2 | 10/2005 | Khuri-Yakub et al. | |
| 7,030,536 B2 | 4/2006 | Smith et al. | |
| 7,037,746 B1 | 5/2006 | Smith et al. | |
| 7,052,464 B2 | 5/2006 | Wodnicki | |
| 7,104,129 B2 | 9/2006 | Nasiri et al. | |
| 7,125,383 B2 | 10/2006 | Hoctor et al. | |
| 7,247,246 B2 | 7/2007 | Nasiri et al. | |
| 7,250,353 B2 | 7/2007 | Nasiri et al. | |
| 7,257,051 B2 | 8/2007 | Thomenius et al. | |
| 7,285,897 B2 | 10/2007 | Fisher et al. | |
| 7,312,440 B2 | 12/2007 | Degertekin et al. | |
| 7,313,053 B2 | 12/2007 | Wodnicki | |
| 7,375,420 B2 | 5/2008 | Fisher et al. | |
| 7,441,321 B2 | 10/2008 | Baumgartner et al. | |
| 7,441,447 B2 | 10/2008 | Degertekin et al. | |
| 7,442,570 B2 | 10/2008 | Nasiri et al. | |
| 7,451,651 B2 | 11/2008 | Woychik et al. | |
| 7,518,251 B2 | 4/2009 | Fisher et al. | |
| 7,530,952 B2 | 5/2009 | Huang et al. | |
| 7,545,012 B2 | 6/2009 | Smith et al. | |
| 7,557,342 B2 | 7/2009 | Federov et al. | |
| 7,564,172 B1 | 7/2009 | Huang | |
| 7,612,483 B2 | 11/2009 | Degertekin | |
| 7,612,635 B2 | 11/2009 | Huang | |
| 7,615,834 B2 | 11/2009 | Khuri-Yakub et al. | |
| 7,622,848 B2 | 11/2009 | Lee et al. | |
| 7,637,149 B2 | 12/2009 | Degertekin et al. | |
| 7,646,133 B2 | 1/2010 | Degertekin | |
| 7,687,976 B2 | 3/2010 | Haider et al. | |
| 7,745,248 B2 | 6/2010 | Park et al. | |
| 7,759,839 B2 | 7/2010 | Huang | |
| 7,764,003 B2 | 7/2010 | Huang | |
| 7,779,696 B2 | 8/2010 | Huang | |
| 7,846,102 B2 | 12/2010 | Kupnik et al. | |
| 7,878,977 B2 | 2/2011 | Mo et al. | |
| 7,880,565 B2 | 2/2011 | Huang | |
| 7,888,709 B2 | 2/2011 | Lemmerhirt et al. | |
| 7,892,176 B2 | 2/2011 | Wodnicki et al. | |
| 7,956,510 B2 | 6/2011 | Huang | |
| 8,004,373 B2 | 8/2011 | Huang | |
| 8,008,105 B2 | 8/2011 | Huang | |
| 8,008,835 B2 | 8/2011 | Degertekin | |
| 8,018,301 B2 | 9/2011 | Huang | |
| 8,076,821 B2 | 12/2011 | Degertekin | |
| 8,105,941 B2 | 1/2012 | Huang | |
| 8,120,229 B2 | 2/2012 | Huang | |
| 8,203,912 B2 | 6/2012 | Roest et al. | |
| 8,222,065 B1 | 7/2012 | Smeys et al. | |
| 8,241,931 B1 | 8/2012 | Antoine et al. | |
| 8,247,945 B2 | 8/2012 | Huang | |
| 8,277,380 B2 | 10/2012 | Daft et al. | |
| 8,309,428 B2 | 11/2012 | Lemmerhirt et al. | |
| 8,315,125 B2 | 11/2012 | Lemmerhirt et al. | |
| 8,324,006 B1* | 12/2012 | Adler .................. B06B 1/0292 257/416 |
| 8,327,521 B2 | 12/2012 | Dirksen et al. | |
| 8,334,133 B2 | 12/2012 | Federov et al. | |
| 8,345,508 B2 | 1/2013 | Wodnicki et al. | |
| 8,345,513 B2 | 1/2013 | Huang | |
| 8,363,514 B2 | 1/2013 | Huang | |
| 8,372,011 B2 | 2/2013 | Degertekin | |
| 8,398,554 B2 | 3/2013 | Degertekin | |
| 8,399,278 B2 | 3/2013 | Lemmerhirt et al. | |
| 8,402,831 B2 | 3/2013 | Kupnik et al. | |
| 8,429,808 B2 | 4/2013 | Huang | |
| 8,451,693 B2 | 5/2013 | Nikoozadeh et al. | |
| 8,483,014 B2 | 7/2013 | Huang | |
| 8,526,271 B2 | 9/2013 | Huang | |
| 8,559,274 B2 | 10/2013 | Huang | |
| 8,563,345 B2 | 10/2013 | Adler et al. | |
| 8,564,076 B1 | 10/2013 | Huang et al. | |
| 8,587,078 B2 | 11/2013 | Huang et al. | |
| 8,647,279 B2 | 2/2014 | Daft et al. | |
| 8,658,453 B2 | 2/2014 | Lemmerhirt et al. | |
| 8,665,672 B2 | 3/2014 | Soeda et al. | |
| 8,957,564 B1* | 2/2015 | Hiroe .................. B06B 1/0292 134/1 |
| 9,061,318 B2 | 6/2015 | Rothberg et al. | |
| 9,067,779 B1* | 6/2015 | Rothberg ............ B81C 1/00238 |
| 9,242,275 B2 | 1/2016 | Rothberg et al. | |
| 9,290,375 B2 | 3/2016 | Rothberg et al. | |
| 9,386,380 B2 | 7/2016 | Chu et al. | |
| 9,394,162 B2 | 7/2016 | Rothberg et al. | |
| 9,499,392 B2 | 11/2016 | Rothberg et al. | |
| 9,499,395 B2 | 11/2016 | Rothberg et al. | |
| 9,505,030 B2 | 11/2016 | Rothberg et al. | |
| 9,533,873 B2 | 1/2017 | Rothberg et al. | |
| 9,718,098 B2 | 8/2017 | Rothberg et al. | |
| 9,738,514 B2 | 8/2017 | Rothberg et al. | |
| 9,895,718 B2 | 2/2018 | Rothberg et al. | |
| 9,899,371 B2 | 2/2018 | Rothberg et al. | |
| 9,910,017 B2 | 3/2018 | Rothberg et al. | |
| 9,910,018 B2 | 3/2018 | Rothberg et al. | |
| 9,944,514 B2 | 4/2018 | Rothberg et al. | |
| 10,175,206 B2 | 1/2019 | Rothberg et al. | |
| 10,177,139 B2 | 1/2019 | Rothberg et al. | |
| 10,228,353 B2 | 3/2019 | Rothberg et al. | |
| 10,247,708 B2 | 4/2019 | Rothberg et al. | |
| 10,266,401 B2 | 4/2019 | Rothberg et al. | |
| 10,272,470 B2 | 4/2019 | Rothberg et al. | |
| 2003/0214029 A1 | 11/2003 | Tao et al. | |
| 2005/0075572 A1 | 4/2005 | Mills et al. | |
| 2005/0121734 A1 | 6/2005 | Degertekin et al. | |
| 2005/0177045 A1 | 8/2005 | Degertekin et al. | |
| 2005/0203397 A1 | 9/2005 | Degertekin | |
| 2005/0248232 A1 | 11/2005 | Itaya et al. | |
| 2006/0116585 A1 | 6/2006 | Nguyen et al. | |
| 2006/0179640 A1 | 8/2006 | Machida et al. | |
| 2006/0230605 A1 | 10/2006 | Schlote-Holubek et al. | |
| 2006/0238067 A1 | 10/2006 | Dausch | |
| 2007/0167811 A1 | 7/2007 | Lemmerhirt et al. | |
| 2007/0167812 A1 | 7/2007 | Lemmerhirt et al. | |
| 2007/0180916 A1 | 8/2007 | Tian et al. | |
| 2007/0190680 A1 | 8/2007 | Fukuda et al. | |
| 2007/0215964 A1 | 9/2007 | Khuri-Yakub et al. | |
| 2007/0262436 A1 | 11/2007 | Kweon et al. | |
| 2008/0138922 A1 | 6/2008 | Wan | |
| 2008/0185669 A1 | 8/2008 | Kok et al. | |
| 2008/0194053 A1 | 8/2008 | Huang | |
| 2008/0290756 A1 | 11/2008 | Huang | |
| 2008/0296708 A1 | 12/2008 | Wodnicki et al. | |
| 2008/0308920 A1 | 12/2008 | Wan | |
| 2009/0069686 A1 | 3/2009 | Daft et al. | |
| 2009/0122651 A1 | 5/2009 | Kupnik et al. | |
| 2009/0133820 A1 | 5/2009 | Sato et al. | |
| 2009/0134497 A1 | 5/2009 | Barth et al. | |

(56) References Cited

U.S. PATENT DOCUMENTS

| | | |
|---|---|---|
| 2009/0148967 A1 | 6/2009 | Wodnicki et al. |
| 2009/0166891 A1 | 7/2009 | Lee et al. |
| 2009/0176375 A1 | 7/2009 | Benson et al. |
| 2009/0250729 A1 | 10/2009 | Lemmerhirt et al. |
| 2010/0027830 A1 | 2/2010 | Hsu et al. |
| 2010/0063397 A1 | 3/2010 | Wagner |
| 2010/0171153 A1 | 7/2010 | Yang |
| 2010/0225200 A1 | 9/2010 | Kupnik et al. |
| 2010/0254222 A1 | 10/2010 | Huang |
| 2011/0055447 A1 | 3/2011 | Costa |
| 2011/0084570 A1 | 4/2011 | Soeda et al. |
| 2011/0115333 A1 | 5/2011 | Ezaki |
| 2011/0140224 A1 | 6/2011 | Kropelnicki et al. |
| 2011/0272693 A1 | 11/2011 | Kobayashi et al. |
| 2012/0074509 A1 | 3/2012 | Berg et al. |
| 2012/0091543 A1 | 4/2012 | Torashima et al. |
| 2012/0129301 A1 | 5/2012 | Or-Bach et al. |
| 2012/0142144 A1 | 6/2012 | Taheri |
| 2012/0187508 A1 | 7/2012 | Adler et al. |
| 2012/0193719 A1 | 8/2012 | Or-Bach et al. |
| 2012/0248554 A1 | 10/2012 | Klein et al. |
| 2013/0087867 A1 | 4/2013 | Ho et al. |
| 2013/0096433 A1 | 4/2013 | Lemmerhirt et al. |
| 2013/0116561 A1 | 5/2013 | Rothberg et al. |
| 2013/0161702 A1 | 6/2013 | Chen |
| 2013/0169110 A1 | 7/2013 | Jeong et al. |
| 2013/0175643 A1 | 7/2013 | Berthelot et al. |
| 2013/0270967 A1 | 10/2013 | Dausch et al. |
| 2013/0301394 A1 | 11/2013 | Chen et al. |
| 2014/0054730 A1 | 2/2014 | Graham et al. |
| 2014/0057382 A1 | 2/2014 | Supino et al. |
| 2014/0183731 A1 | 7/2014 | Lin et al. |
| 2014/0217478 A1 | 8/2014 | Rothberg et al. |
| 2014/0219062 A1 | 8/2014 | Rothberg et al. |
| 2014/0264474 A1 | 9/2014 | Chu et al. |
| 2014/0264660 A1 | 9/2014 | Rothberg et al. |
| 2014/0355381 A1 | 12/2014 | Lal et al. |
| 2015/0084053 A1 | 3/2015 | Rothberg et al. |
| 2015/0097215 A1* | 4/2015 | Chu .................. B81C 1/00238 257/254 |
| 2015/0137285 A1 | 5/2015 | Shim et al. |
| 2015/0156571 A1 | 6/2015 | Shim et al. |
| 2015/0175406 A1 | 6/2015 | Lin et al. |
| 2015/0251895 A1* | 9/2015 | Chu .................. B81C 1/00238 257/595 |
| 2015/0251896 A1 | 9/2015 | Rothberg et al. |
| 2015/0298170 A1 | 10/2015 | Rothberg et al. |
| 2016/0009544 A1 | 1/2016 | Rothberg et al. |
| 2016/0009549 A1 | 1/2016 | Rothberg et al. |
| 2016/0207760 A1 | 7/2016 | Rothberg et al. |
| 2016/0264400 A1 | 9/2016 | Rothberg et al. |
| 2016/0280538 A1 | 9/2016 | Rothberg et al. |
| 2016/0290969 A1 | 10/2016 | Rothberg et al. |
| 2016/0290970 A1 | 10/2016 | Rothberg et al. |
| 2016/0379973 A1 | 12/2016 | Rothberg et al. |
| 2017/0029271 A1 | 2/2017 | Rothberg et al. |
| 2017/0056926 A1 | 3/2017 | Rothberg et al. |
| 2017/0225196 A1 | 8/2017 | Rothberg et al. |
| 2017/0283254 A1 | 10/2017 | Rothberg et al. |
| 2017/0315099 A1 | 11/2017 | Rothberg et al. |
| 2018/0003678 A1 | 1/2018 | Rothberg et al. |
| 2018/0130795 A1 | 5/2018 | Rothberg et al. |
| 2018/0133756 A1 | 5/2018 | Rothberg et al. |
| 2018/0186628 A1 | 7/2018 | Rothberg et al. |
| 2018/0364201 A1 | 12/2018 | Rothberg et al. |
| 2019/0160490 A1 | 5/2019 | Rothberg et al. |
| 2019/0164956 A1 | 5/2019 | Rothberg et al. |
| 2019/0210869 A1 | 7/2019 | Rothberg et al. |

FOREIGN PATENT DOCUMENTS

| | | |
|---|---|---|
| CN | 101640834 A | 2/2010 |
| EP | 1 225 984 B1 | 11/2004 |
| EP | 2 441 530 A2 | 4/2012 |
| GB | 2 467 776 A | 8/2010 |
| JP | 2005-103294 A | 4/2005 |
| JP | 2006-211185 A2 | 8/2006 |
| JP | 2007-215177 A2 | 8/2007 |
| JP | 2009-503918 T | 1/2009 |
| JP | 2010-035134 A | 2/2010 |
| JP | 2010-172181 A | 8/2010 |
| JP | 2010-240825 A | 10/2010 |
| JP | 2011-045040 A | 3/2011 |
| JP | 2011-109358 A | 6/2011 |
| JP | 2011-522444 T2 | 7/2011 |
| JP | 2012-085239 A2 | 4/2012 |
| JP | 2012-519958 T2 | 8/2012 |
| JP | 2013-138411 A | 7/2013 |
| KR | 10-2013-0134724 A | 12/2013 |
| TW | 201409583 A | 3/2014 |
| WO | WO 2006/123299 A2 | 11/2006 |
| WO | WO 2009/073562 A1 | 6/2009 |
| WO | WO 2009/107940 A2 | 9/2009 |
| WO | WO 2012/017978 A2 | 2/2012 |
| WO | WO 2014/151525 A2 | 9/2014 |

OTHER PUBLICATIONS

U.S. Appl. No. 16/364,388, filed Mar. 26, 2019, Rothberg et al.
U.S. Appl. No. 16/290,188, filed Mar. 1, 2019, Rothberg et al.
U.S. Appl. No. 16/245,214, filed Jan. 10, 2019, Alie et al.
International Search Report and Written Opinion dated Jul. 1, 2014 for Application No. PCT/US2014/014705.
International Preliminary Report on Patentability dated Aug. 20, 2015 for Application No. PCT/US2014/014705.
Invitation to Pay Additional Fees dated Nov. 6, 2014 for Application No. PCT/US2014/025924.
International Search Report and Written Opinion dated Feb. 18, 2015 for Application No. PCT/US2014/025924.
International Preliminary Report on Patentability dated Sep. 24, 2015 for Application No. PCT/US2014/025924.
International Search Report and Written Opinion dated Jun. 29, 2015 for Application No. PCT/US2015/026290.
International Preliminary Report on Patentability dated Oct. 27, 2016 for Application No. PCT/US2015/026290.
International Search Report and Written Opinion dated Oct. 29, 2015 for Application No. PCT/US2015/040342.
International Preliminary Report on Patentability dated Jan. 26, 2017 for Application No. PCT/US2015/040342.
Office Communication dated Feb. 13, 2015 for U.S. Appl. No. 14/172,383.
Office Communication dated May 15, 2015 for U.S. Appl. No. 14/635,197.
Office Communication dated May 21, 2015 for U.S. Appl. No. 14/208,351.
Notice of Allowance dated Sep. 14, 2015 for U.S. Appl. No. 14/208,351.
Notice of Allowance dated Nov. 10, 2015 for U.S. Appl. No. 14/711,145.
Notice of Allowance dated Dec. 4, 2015 for U.S. Appl. No. 14/172,383.
Office Communication dated Dec. 16, 2015 for U.S. Appl. No. 14/716,152.
Office Communication dated Jul. 12, 2016 for U.S. Appl. No. 14/172,840.
[No Author Listed], Sil-Via, TSI & Advanced Features. Silex Microsystems. http://www.silexmicrosystems.com/mems-foundry/sil-via-tsi-advanced-features/ [last accessed Jan. 6, 2015]. 4 pages.
Calmes et al., Highly Integrated 2-D Capacitive Micromachined Ultrasonic Transducers. 1999 IEEE Ultrason Symp. 1999;1163-6.
Cha et al., Influences of perforation ratio in characteristics of capacitive micromachined ultrasonic transducers in air. Sensors Actuators A. 2011;171:191-8.
Cheng et al., An Efficient Electrical Addressing Method Using Through-Wafer Vias for Two-Dimensional Ultrasonic Arrays. 2000 IEEE Ultrasonics Symposium. 2000;2:1179-82.

(56) References Cited

OTHER PUBLICATIONS

Cheng et al., Electrical Through-Wafer Interconnects with Sub-PicoFarad Parasitic Capacitance. 2001 Microelectromechan Syst Conf. Aug. 24, 2001;18-21.

Daft et al., Microfabricated ultrasonic transducers monolithically integrated with high voltage electronics. Proc Ultrason Symp. 2004;493-6.

Dixon-Warren, Overview of MEMS microphone technologies for consumer applications. MEMS J. Mar. 8, 2011. http://www.memsjournal.com/2011/03/overview-of-mems-microphone-technologies-for-consumer-applications.html [last accessed Feb. 19, 2014]. 10 pages.

Doody et al., Modeling and Characterization of CMOS-Fabricated Capacitive Micromachined Ultrasound Transducers. J Microelectromech Sys. Feb. 1, 2011;20(1):104-18.

Eccardt et al., Micromachined ultrasound transducers with improved coupling factors from a CMOS compatible process. Ultrasonics. Mar. 2000;38:774-80.

Eccardt et al., Surface micromachined ultrasound transducer in CMOS technology. Proc Ultrason Symp. 1996;959-62.

Gurun et al., Front-end CMOS electronics for monolithic integration with CMUT arrays: circuit design and initial experimental results. Proc Ultrason Symp. 2008;390-3.

Helin et al., Poly-SiGe-based CMUT array with high acoustical pressure. MEMS. 2012 IEEE 25th International Conference on Micro Electro Mechanical Systems. Jan. 29, 2012;305-8.

Kim et al., Design and Test of a Fully Controllable 64×128 2-D CMUT Array Integrated with Reconfigurable Frontend ASICs for Volumetric Ultrasound Imaging. IEEE. International Ultrasonics Symposium Proceedings. Oct. 7-10, 2012;77-80. doi: 10.1109/ULTSYM.2012.0019.

Knight et al., Low Temperature Fabrication of Immersion Capacitive Micromachined Ultrasonic Transducers on Silicon and Dielectric Substrates. IEEE Trans Ultrason Ferroelectr Freq Contr. Oct. 2004;51(10):1324-33.

Kupnik et al., CMUT Fabrication Based on a Thick Buried Oxide Layer. Proc IEEE Ultrason Symp. Oct. 2010;2010:547-550. doi:10.1109/ULTSYM.2010.5935935. Epub Jun. 8, 2012. 10 pages.

Kupnik et al., Wafer-Bonded CMUT Meets CMOS. 2010 CMOS Emerging Technology Workshop. May 21, 2010;1-22.

Lemmerhirt et al., A 32×32 capacitive micromachined ultrasonic transducer array manufactured in standard CMOS. IEEE Trans Ultrason Ferroelectr Freq Control. Jul. 2012;59(7):1521-36. doi: 10.1109/TUFFC.2012.2352.

Lemmerhirt et al., An electronically-scanned CMUT-in-CMOS transducer for hemodialysis vascular access monitoring. Ultrason Symp. 2011 IEEE International Conference. Oct. 18, 2011;2193-6.

Lin et al., Packaging of Large and Low-Pitch Size 2D Ultrasonic Transducer Arrays. MEMS Conf. 2010;508-11.

Lu et al., Investigation of thermal stress influence on CMUT in standard CMOS process. Info Auto. 2009 ICIA International Conference. Jun. 22, 2009;1447-51.

Manzanares et al., Air-coupled MUMPs capacitive micromachined ultrasonic transducers with resonant cavities. Ultrason. 2012;52:482-9.

Nikoozadeh et al., Forward-Looking Intracardiac Ultrasound Imaging Using a 1-D CMUT Array Integrated With Custom Front-End Electronics. IEEE Trans Ultrason Ferroelectr Freq Contr. Dec. 2008;55(12):2651-60.

Noble et al., A cost-effective and manufacturable route to the fabrication of high-density 2D micromachined ultrasonic transducer arrays and (CMOS) signal conditioning electronics on the same silicon substrate. Proc Ultrason Symp. 2001;941-5.

Noble et al., Low-temperature micromachined CMUTs with fully-integrated analogue front-end electronics. Proc Ultrason Symp. 2002;1045-50.

Oralkan et al., Volumetric Imaging Using 2D Capacitive Micromachined Ultrasonic Transducer Arrays (CMUTs): Initial Results. 2002 IEEE Ultrason Symp. 2002;1083-6.

Oralkan et al., Volumetric Ultrasound Imaging Using 2-D CMUT Arrays. IEEE Trans Ultrason Ferroelectr Freq Contr. Nov. 2003;50(11):1581-94.

Park et al., Fabrication of Capacitive Micromachined Ultrasonic Transducers via Local Oxidation and Direct Wafer Bonding. J Microelectromechan Syst. Feb. 2011;20(1):95-103.

Torkkeli et al., Capacitative microphone with low-stress polysilicon membrane and high-stress polysilicon backplate. Sensors and Actuators. 2000;85:116-23.

Tsuji et al., Low Temperature Process for CMUT Fabrication with Wafer Bonding Technique. IEEE Intl Ultrason Symp Proc. 2010;551-4.

Um et al., An Analog-Digital-Hybrid Single-Chip RX Beamformer with Non-Uniform Sampling for 2D-CMUT Ultrasound Imaging to Achieve Wide Dynamic Range of Delay and Small Chip Area. IEEE International Solid-State Circuits Conference. Feb. 12, 2014;426-8.

Wodnicki et al., Multi-Row Linear CMUT Array Using CMUTs and Multiplexing Electronics. Proc Ultrason Symp. 2009;2696-9.

Wolffenbuttel et al., Low-temperature silicon wafer-to-wafer bonding using gold at eutectic temperature. Sensors and Actuators A. 1994;43:223-9.

Wygant et al., Integration of 2D CMUT Arrays with Front-End Electronics for Volumetric Ultrasound Imaging. IEEE Trans Ultrason Ferroelectr Freq Contr. Feb. 2008;55(2):327-42.

Xu et al., Characterization of improved Capacitive Micromachined Ultrasonic Transducers (CMUTS) using ALD high-[Kappa] dielectric isola. MEMS. 2014 IEEE 27th International Conference on Micro Electro Mechanical Systems. Jan. 26, 2014;584-7.

Yu et al., Dual-bottom-electrode CMUT based on standard CMOS process. NEMS. 2001 IEEE International Conference. Feb. 20, 2011;21-4.

Zahorian et al., Single chip CMUT arrays with integrated CMOS electronics: fabrication process development and experimental results. Proc Ultrason Symp. 2008;386-9.

Zhuang et al., Integration of trench-isolated through-wafer interconnects with 2d capacitive micromachined ultrasonic transducer arrays. Sensors Actuators A. 2007;138:221-9.

Zhuang et al., Wafer-bonded 2-D CMUT arrays incorporating through-wafer trench-isolated interconnects with a supporting frame. IEEE Trans Ultrason Ferroelectr Freq Control. Jan. 2009;56(1):182-92. doi: 10.1109/TUFFC.2009.1018.

\* cited by examiner

MICROFABRICATED ULTRASONIC TRANSDUCER HAVING INDIVIDUAL CELLS WITH ELECTRICALLY ISOLATED ELECTRODE SECTIONS

CROSS-REFERENCE TO RELATED APPLICATIONS

This application claims the benefit under 35 U.S.C. § 119(e) of U.S. Provisional Application Ser. No. 62/522,875, filed on Jun. 21, 2017 entitled "MICROFABRICATED ULTRASONIC TRANSDUCER HAVING INDIVIDUAL CELLS WITH ELECTRICALLY ISOLATED ELECTRODE SECTIONS," which is hereby incorporated herein by reference in its entirety.

BACKGROUND

The present disclosure relates generally to ultrasound imaging. In particular, the present disclosure relates to Capacitive Micromachined Ultrasonic Transducers (CMUTs) and CMUT transducers having individual cells with electrically isolated electrode sections, and methods for forming the same.

Capacitive Micromachined Ultrasonic Transducers (CMUTs) are known devices that include a membrane above a micromachined cavity. The membrane may be used to transduce an acoustic signal into an electric signal, or vice versa. Thus, CMUTs can operate as ultrasonic transducers.

Two types of processes can be used to fabricate CMUTs. Sacrificial layer processes form the membrane of the CMUT on a first substrate above a sacrificial layer. Removal of the sacrificial layer results in the membrane being suspended above a cavity. Wafer bonding processes bond two wafers together to form a cavity with a membrane.

SUMMARY

In one aspect, an apparatus is provided, comprising: an ultrasonic transducer substrate having a membrane, a bottom electrode, and a plurality of cavities disposed between the membrane and the bottom electrode, each of the plurality of cavities corresponding to an individual transducer cell; wherein portions of the bottom electrode corresponding to each individual transducer cell are electrically isolated from one another; and each portion of the bottom electrode corresponding to each individual transducer cell further comprising a first bottom electrode portion and a second bottom electrode portion, the first and second bottom electrode portions electrically isolated from one another.

In another aspect, an ultrasound device is provided, comprising an engineered substrate comprising first and second substrates bonded together to define a plurality of cavities, each cavity corresponding to an individual ultrasound transducer cell; and an electrical substrate bonded to the engineered substrate; wherein the first substrate comprises a bottom electrode for each individual transducer cell, with portions of the bottom electrode corresponding to each individual transducer cell being electrically isolated from one another; and each portion of the bottom electrode corresponding to each individual transducer cell further comprising a first bottom electrode portion and a second bottom electrode portion, the first and second bottom electrode portions electrically isolated from one another.

In another aspect, a method, comprising: forming a plurality of cavities in a first side of a first substrate; for one or more of the plurality of cavities, forming first isolation trenches in the first side of the first substrate; bonding a second substrate to the first substrate to seal the cavities; and forming second isolation trenches in a second side of the first substrate; the bonded first and second substrates defining an ultrasonic transducer substrate having a membrane, a bottom electrode, and the plurality of cavities disposed between the membrane and the bottom electrode, each of the plurality of cavities corresponding to an individual transducer cell; wherein portions of the bottom electrode corresponding to each individual transducer cell are electrically isolated from one another by the second isolation trenches; and each portion of the bottom electrode corresponding to each individual transducer cell further comprising a first bottom electrode portion and a second bottom electrode portion, the first and second bottom electrode portions electrically isolated from one another by the first isolation trenches.

In another aspect, a method of forming an ultrasound device, the method comprising: forming a plurality of cavities in a first side of a first substrate; for one or more of the plurality of cavities, forming first isolation trenches in the first side of the first substrate; bonding a second substrate to the first substrate to seal the cavities; forming second isolation trenches in a second side of the first substrate; the bonded first and second substrates defining an engineered substrate having a membrane, a bottom electrode, and the plurality of cavities disposed between the membrane and the bottom electrode, each of the plurality of cavities corresponding to an individual ultrasound transducer cell; wherein portions of the bottom electrode corresponding to each individual transducer cell are electrically isolated from one another by the second isolation trenches, and wherein each portion of the bottom electrode corresponds to each individual transducer cell that further comprises a first bottom electrode portion and a second bottom electrode portion, the first and second bottom electrode portions electrically isolated from one another by the first isolation trenches; and bonding the engineered substrate to an electrical substrate.

BRIEF DESCRIPTION OF THE DRAWINGS

Various aspects and embodiments of the application will be described with reference to the following figures. It should be appreciated that the figures are not necessarily drawn to scale. Items appearing in multiple figures are indicated by the same reference number in all the figures in which they appear.

DETAILED DESCRIPTION

Figure 1:
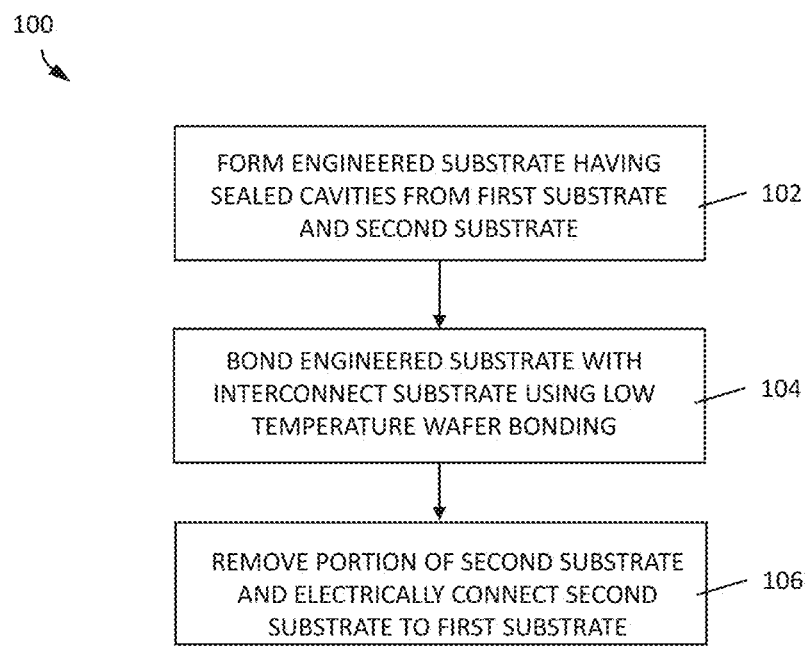
FIG. 1 is a flowchart of a fabrication sequence for fabricating an engineered transducer substrate integrated with an electrical substrate such as CMOS wafer, according to a non-limiting embodiment of the present application.

Aspects of the present application relate to fabrication and integration of CMUT substrates with electrical substrates such as CMOS wafers, thereby forming CMOS ultrasonic transducers (CUTs). The methods described provide scalable, low cost, high yield solutions to the challenge of integrating CMUTs with CMOS wafers using techniques available in commercial semiconductor foundries, thus utilizing a readily available supply chain.

According to an aspect of the present application, a MEMS design and process provides trench isolation surrounding each individual transducer cell, creating an electrically isolated bottom electrode for each transducer cell. At least some advantages of adding trench isolation inside a cell cavity include the reduction of parasitic capacitance by isolating the pinned, nonactive regions around the cell's outer diameter. In addition, a dual electrode CUT cell may be implemented such that an intracavity trench structure may segment each cell's bottom electrode into dual electrodes, which can then be electrically addressed individually. In turn, one exemplary application for such a dual electrode structure is to have separate transmit and receive regions within a single cell, choosing the optimal regions for each function. Moreover, separate transmit and receive electrodes may enable simultaneous operation, and eliminating the need for a transmit/receive (T/R) switch which may be a contributor to system noise.

According to an aspect of the present application, a wafer-level process is presented involving two wafer bonding steps, at least one of which may take advantage of wafer level packaging techniques. A first wafer bonding step may form sealed cavities by bonding together a silicon-on-insulator (SOI) wafer and a bulk silicon wafer, the resulting bonded structure being considered an engineered substrate. Relatively high temperatures may be used, for example during an anneal, to facilitate achieving a strong bond. The bulk silicon wafer of the engineered substrate may then be thinned, after which a second wafer bonding step may be performed to bond the engineered substrate with an electrical substrate such as, for example, a CMOS wafer having integrated circuits (ICs) formed thereon. The second wafer bonding step may use a relatively low temperature to avoid damage to the ICs on the CMOS wafer. The handle layer of the SOI wafer of the engineered substrate may then be removed. In addition to CMOS wafers or substrates, the term "electrical substrate" may also include, but is not necessarily limited to, substrates such as analog circuit substrates, application specific integrated circuit (ASIC) substrates, interposer substrates, printed circuit board (PCB) substrates, flexible substrates, and the like.

In some embodiments, the bonding used to form the engineered substrate with sealed cavities may include fusion bonding. In some such embodiments, the bonding may be performed at a low temperature. However, a relatively high temperature anneal may be performed to ensure a strong bond. The fabrication of sealed cavities is decoupled from the thermal budget of CMOS IC fabrication since the engineered substrate is fabricated prior to integrating such structures with a CMOS wafer, thus allowing for use of a relatively high temperature anneal for high bond strength without damaging ICs in the final device. As described in further detail below, in some embodiments, oxide quality of layers used in the fusion bonding are optimize for improved device performance.

In some embodiments, the bonding performed to integrate the engineered substrate having sealed cavities with the CMOS wafer may include thermal compression (also referred to herein as "thermocompression"), eutectic bonding, or silicide bonding (which is a bond formed by bringing silicon of one substrate into contact with metal on a second substrate under sufficient pressure and temperature to form a metal silicide, creating a mechanical and electrical bond), as non-limiting examples. Such bonding may be performed at temperatures sufficiently low to avoid damage to the ICs on the CMOS wafer, while still providing for a strong bond and also facilitating electrical interconnection of the ICs on the CMOS wafer with the sealed cavities of the engineered substrate. Accordingly, aspects of the present application implement low temperature (e.g., below 450° C.) wafer bonding to form ultrasonic transducer membranes on CMOS wafers. Low temperature in this context may, in some embodiments, be below 450° C., below 400° C., below 350° C., between 200° C. and 450° C., any temperature within that range, or any suitable temperature for preserving structures on a CMOS wafer. Thus, the bonding processes as well as other fabrication steps for integrating the sealed cavities with CMOS ICs to form CUTs may avoid any anneals above 450° C.

According to an aspect of the present application, an apparatus including an engineered substrate is bonded with an electrical substrate such as a CMOS wafer having a CMOS IC formed thereon. The engineered substrate may include multiple wafers bonded together to form sealed cavities. The engineered substrate may then be bonded with the CMOS wafer. The engineered substrate may include one substrate configured to serve as a membrane which vibrates and another substrate serving as a support, and which is not meant to vibrate within an operating frequency range of the device. This latter substrate may be sufficiently thick (e.g., greater than approximately 5 microns) to prevent unwanted vibration, but also sufficiently thin (e.g., less than approximately 30-50 microns) to contribute to small device dimensions. The engineered substrate may also use highly doped silicon to serves as conductive CUT electrodes.

According to an aspect of the present application, an apparatus including an engineered substrate is bonded with an electrical substrate such as a CMOS wafer having a CMOS IC formed thereon and the engineered substrate includes multiple wafers bonded together to form sealed cavities and configured to vibrate. One wafer of the engineered substrate may be configured to resonate at a first frequency and a second wafer of the engineered substrate may be configured to resonate at a different frequency. Thus, a multi-frequency ultrasound transducer may be created. One frequency may be used for transmit operations and the other for receive operations, as a non-limiting example. For example, a first, lower frequency may be used for transmit operations and a second, higher frequency (e.g., twice the frequency of the lower frequency) may be used for receive operations, as a non-limiting example.

The aspects and embodiments described above, as well as additional aspects and embodiments, are described further below. These aspects and/or embodiments may be used individually, all together, or in any combination of two or more, as the application is not limited in this respect.

The term "SOI wafer" as used herein has its conventional meaning, including a handle layer, a buried oxide (BOX) layer, and a silicon device layer separated from the handle layer by the BOX layer.

The term "engineered substrate" as used herein refers to a substrate engineered to differ from a basic silicon wafer or standard SOI wafer. An engineered substrate may also be a "composite substrate" formed by combining multiple distinct elements (e.g., multiple distinct wafers). Examples of engineered substrates may include, but are not limited to, CMUT substrates and PMUT (piezoelectric micromachined ultrasonic transducer) substrates. Integrated approaches described herein allow for such various types of engineered substrates, as thermal budgets for forming the same are decoupled from an integrated circuit (e.g., CMOS) thermal budgets.

Throughout this disclosure, the use of the term "approximately" includes "exactly" unless context dictates otherwise. For example, describing a distance as being less than approximately 10 microns ($\mu m$) is to be understood to include the scenario in which the distance is less than or equal to 10 $\mu m$.

As described, aspects of the present application provide a process for fabricating CUTs having integrated CMUTs and CMOS ICs and utilizing two separate bonding steps. The process may allow for a resulting structure to include a relatively thin engineered substrate having cavities formed between two silicon layers monolithically integrated with a CMOS wafer having CMOS ICs thereon. FIG. 1 illustrates an example of the process.

As shown, the method 100 may begin at operation 102 with the formation of an engineered substrate having sealed cavities. Two substrates or wafers (e.g., a first substrate comprising a bulk silicon wafer and a second substrate comprising an SOI wafer) may be bonded together, for example with high quality oxide layers of the two wafers facing each other. One (or both) of the two wafers may have a plurality of cavities formed therein, such that bonding the two wafers together may result in sealed cavities suitable for use as the cavities of CMUTs (or as stated previously, PMUTs, for example). To ensure a strong bond between the two wafers, high temperature processing may be used. For example, a high temperature anneal may be used subsequent to a low temperature wafer bond, such as a low temperature fusion bond. Thus, a combination of high and low temperatures may be used in forming the engineered substrate in some embodiments. High temperature in this context may, in some embodiments, be above 450° C., a temperature threshold above which CMOS ICs would typically be damaged.

The bonding of the two wafers may be performed in vacuum so that the resulting sealed cavities have a low pressure (e.g., a pressure between approximately $1 \times 10^{-3}$ Torr and approximately $1 \times 10^{-5}$ Torr, a pressure less than approximately 1 atmosphere, or any other suitable pressure). In some embodiments, the bond is performed in an inert ambient, for example using $N_2$. At operation 104, a handle layer of a first wafer (if the first wafer is an SOI wafer) of the two wafers may be removed, in any suitable manner, such as by a combination of grinding followed by etching, or the first layer may be thinned (if the first wafer is a bulk silicon layer).

At operation 104, the engineered substrate may be bonded with an electrical substrate (e.g., a CMOS wafer having integrated circuitry) to form an integrated device. The bonding may be performed at temperatures below 450° C. to prevent damage to the electrical substrate (e.g., the circuitry of the CMOS wafer). In some embodiments, thermocompression bonding is used, although alternatives including eutectic bonding and silicide bonding are also possible, among others.

At operation 106, a portion of the second substrate of the engineered substrate may be thinned (e.g., by removing a handle layer of the SOI wafer of the engineered substrate) may be removed, for example, by a combination of grinding followed by etching. As a result, in some embodiments, the engineered substrate may include only two silicon layers between which are the cavities. Having only two silicon layers may, among other benefits, facilitate achieving thin dimensions for the engineered substrate. For example, the engineered substrate at this stage may be relatively thin, for example being less than 100 $\mu m$ in total thickness, less than 50 $\mu m$ in total thickness, less than 30 $\mu m$ in total thickness, less than 20 $\mu m$ in total thickness, less than 10 $\mu m$ in total thickness (e.g., approximately 8 $\mu m$ or approximately 5 $\mu m$), or any other suitable thickness. Structures with such small thicknesses lack sufficient structural rigidity to survive many fabrication processes, including wafer bonding. Thus, according to some embodiments of the present application, the engineered substrate is not reduced to such dimensions until after bonding with the CMOS wafer, which can provide mechanical support to the engineered substrate. Moreover, in some embodiments it is preferable for one of the two wafers of the engineered substrate to be sufficiently thick to minimize or prevent vibration of that wafer at the operating frequencies. The vibrating membrane of the engineered substrate may have a thickness of at least, for example, 4 $\mu m$ in some embodiments, at least 5 $\mu m$ in some embodiments, at least 7 $\mu m$ in some embodiments, at least 10 $\mu m$ in some embodiments, or other suitable thickness.

As further illustrated at operation 106, the second substrate of the engineered substrate may be electrically connected to the first substrate of the engineered substrate, and electrical connections may be made between the ICs on the CMOS wafer (or more generally the electrical substrate) and the sealed cavities of the engineered substrate to provide functioning ultrasonic transducers. For example, the silicon device layer of the engineered substrate proximate the CMOS wafer may serve as a bottom electrode for the ultrasonic transducers while the silicon device layer distal the CMOS wafer may serve as a membrane, and electrical connections may be made to these structures as appropriate to control operation of the membrane (e.g., to actuate (or induce vibration of) the membrane by applying a voltage). In some embodiments, electrical connection may be made (or may be at least partially completed) between the engineered substrate and the CMOS wafer using conductive bonding materials (e.g., metals, highly doped silicon or polysilicon) which serve as both bonding materials and electrical connections. Alternatively, or additionally, electrical connections may be made subsequent to bonding of the engineered substrate with the CMOS wafer. For example, bonding the engineered substrate with the CMOS wafer may form electrical connections to a bottom electrode of the ultrasonic transducer, and on-chip metal electrical and/or wire bonds may be formed subsequently to provide electrical connection to top electrodes or membrane of the ultrasonic transducer.

Figure 2:
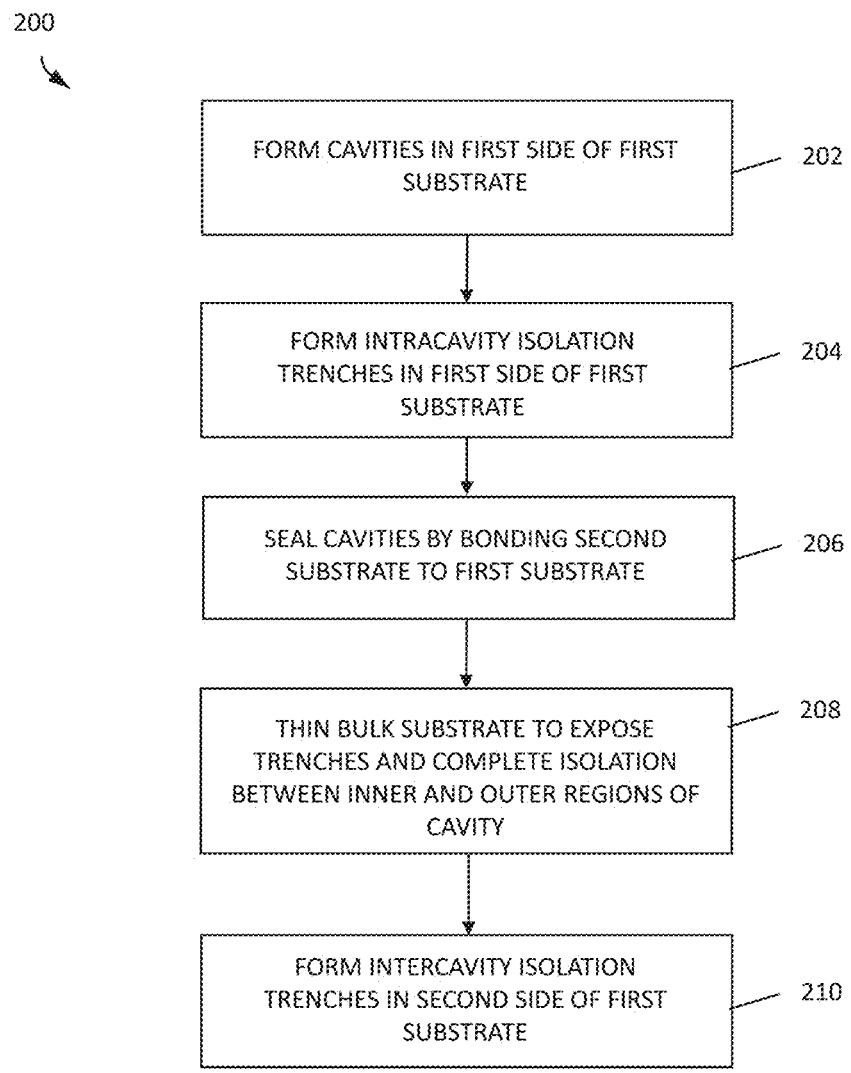
FIG. 2 is a flowchart illustrating a detailed example of a stage of the process of FIG. 1, for fabricating an engineered substrate having trench isolation inside an individual cell cavity, according to a non-limiting embodiment of the present application.

FIG. 2 illustrates further detail with respect to one example of the implementation of operation 102 of method 100, for fabricating an engineered substrate having trench isolation inside an individual cell cavity, according to a non-limiting embodiment of the present application.

In operation 202, cavities may be formed in a first side of a first substrate. Here, this may be accomplished by etching a bulk silicon wafer, following by forming a quality oxide layer (e.g., thermal oxide) over the bulk silicon wafer and cavities. It should be appreciated that a thermal oxide represents a non-limiting example of an oxide, and that other types of oxides may alternatively be formed. Furthermore, a "quality oxide" as described herein may have one or more of the following characteristics: a pure stoichiometric $SiO_2$; no residual chemistry (e.g., traces of reactants from PECVD); mechanically stable and dense (e.g., no further densification resulting from subsequent high temperature processes); any metallic contaminants near or below detection limits (e.g., $10^{10}$-$10^{15}$ atoms/cm$^2$, depending upon technique); mobile ion contaminants (e.g., Na, Li, Ca, K) near or below detection limits (e.g., about $10^{10}$ atoms/cm$^2$); minimal to no dopant incorporation (e.g., from substrate autodoping); dopant incorporation well below $10^{15}$ atoms/cm$^2$; no trapped states or trapped charge; a high quality Si—$SiO_2$ interface (e.g., no trapped charge or interface states); no surface contamination (organic or other); low particle counts; uniform thickness and refractive index.

Then, at operation 204, additional processing is performed to define intracavity isolation trenches. That is, within the footprint of an individual cavity, one or more isolation trenches may be further defined by etching narrow trenches deeper into a first side of the first substrate (i.e., the same side of the first substrate that the cavities are formed). As is further described in greater detail below, the narrow trenches within the cavity footprint may be filled with an insulating material to electrically isolate portions of the bottom electrode of the transducer cell.

At operation 206, the cavities may be sealed by bonding a second substrate to the first substrate. This may be accomplished by, for example, using a low temperature fusion bond. In some embodiments, the second substrate may include a quality oxide layer formed on the silicon device layer of an SOI wafer, such that bonding the first and second substrates together may involve making direct contact with oxide layers of the substrates, thus forming a $SiO_2$—$SiO_2$ bond.

As a result of bonding the two substrates together, the cavities in the first substrate may be sealed. For example, the cavities may be vacuum sealed in some embodiments, although in other embodiments a vacuum seal may not be formed. An anneal may then be performed to facilitate formation of a strong bond between the two substrates. As described previously, in some embodiments the anneal may be a high temperature anneal, for example being performed between approximately 500° C. and approximately 1,500° C. (e.g., 500° C., 750° C., 1,000° C., 1,250° C.), including any temperature or range of temperatures within that range (e.g., between approximately 500° C. and approximately 1,200° C.), although other temperatures may alternatively be used. In some embodiments, an anneal may be performed between approximately 300° C. and approximately 1,200° C.

Then, at operation 208, the bulk substrate is thinned in order to expose the isolation trenches and complete isolation between inner and outer regions of the cavity. Subsequently, intercavity isolation trenches may be formed in a second side of the first substrate, as illustrated in operation 210.

Figure 3A:
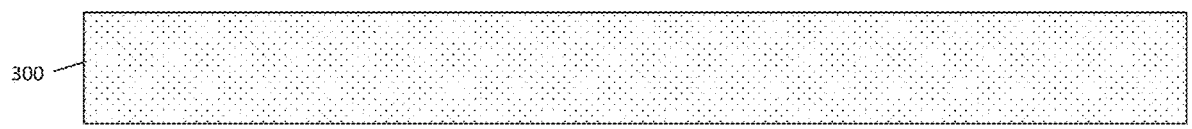
FIGS. 3A-3S illustrate a fabrication sequence for forming the engineered substrate of FIG. 1 and FIG. 2, according to a non-limiting embodiment of the present application.
Figure 3B:
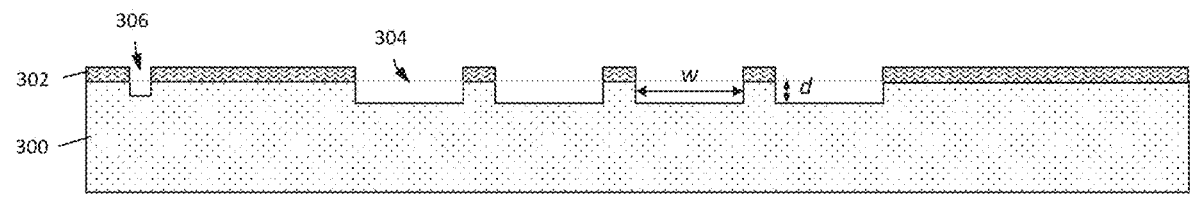
Figure 3C:
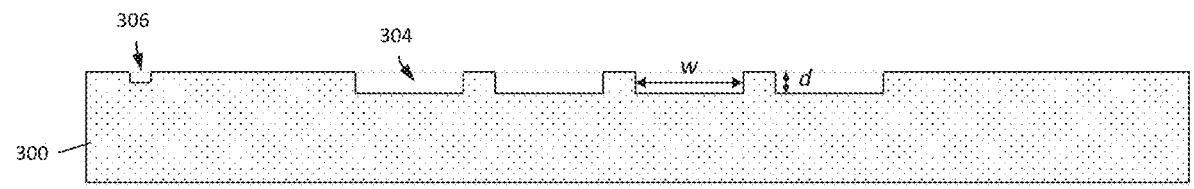
Figure 3D:
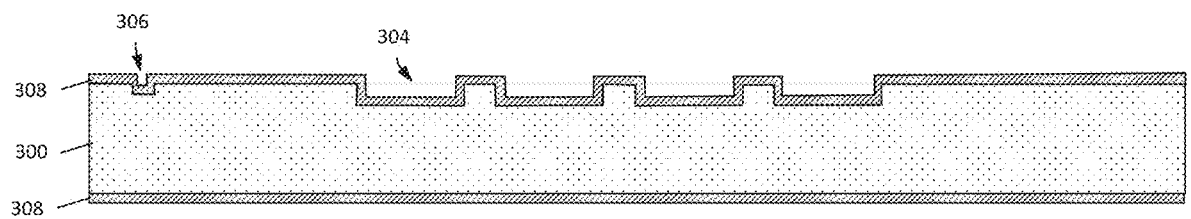
Figure 3E:
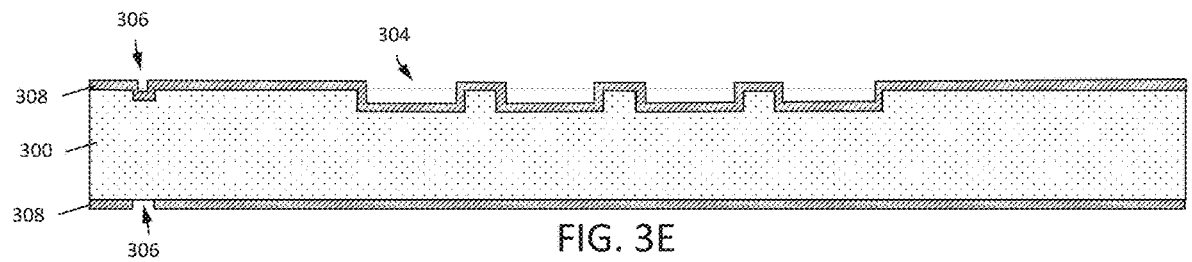
Figure 3F:
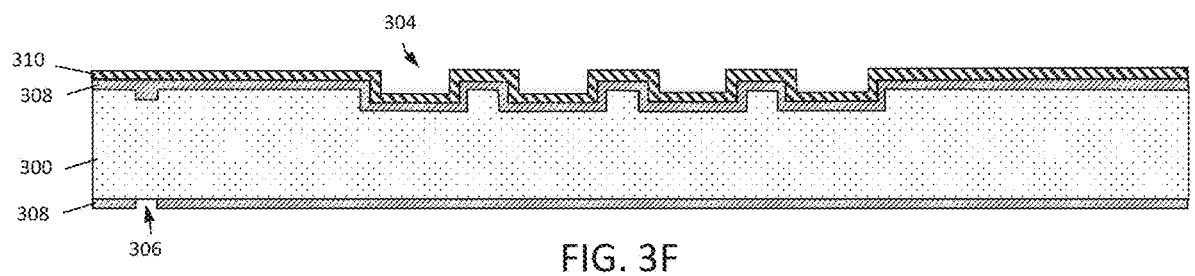
Figure 3G:
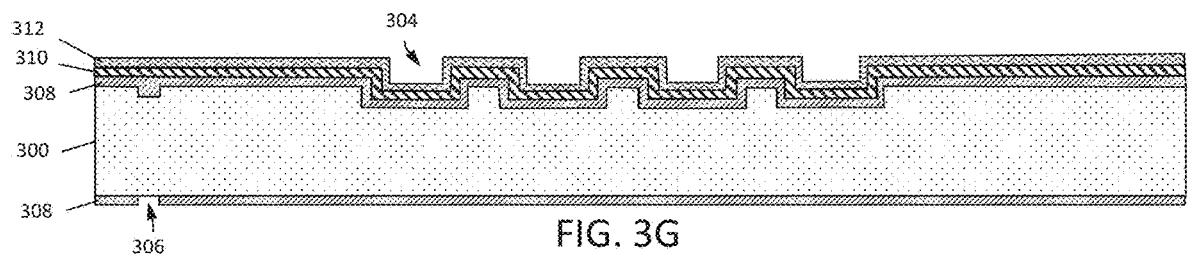
Figure 3H:
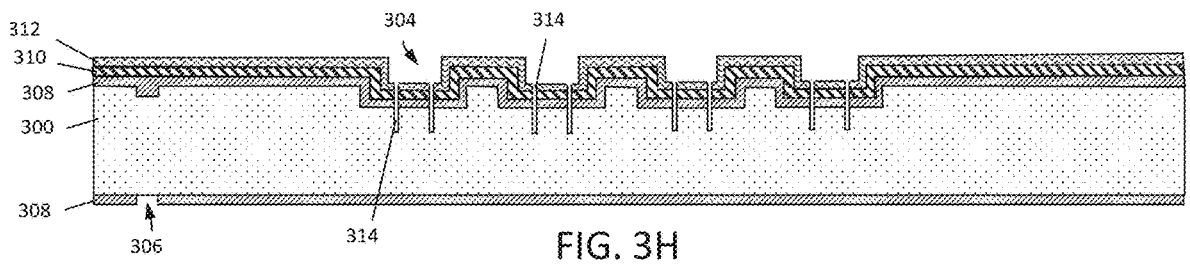
Figure 3I:
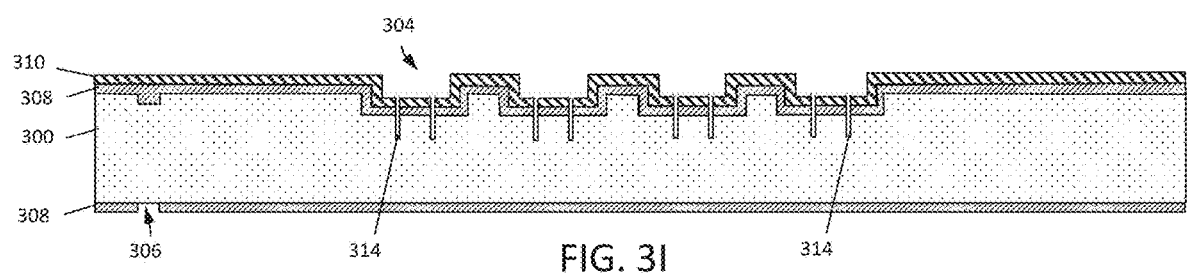
Figure 3J:
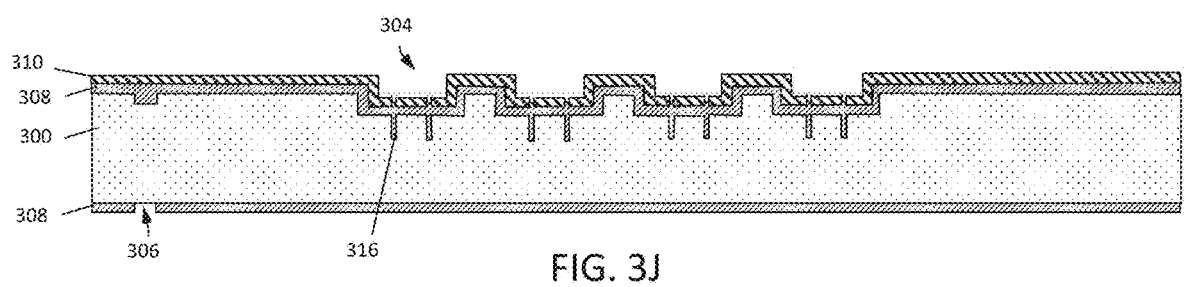
Figure 3K:
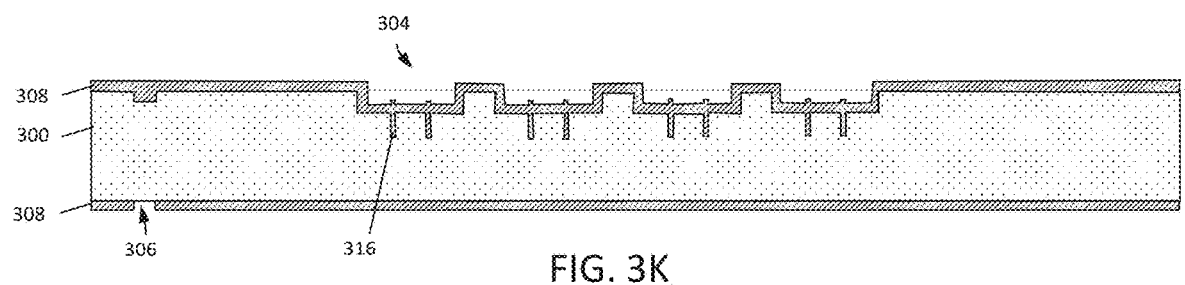
Figure 3L:
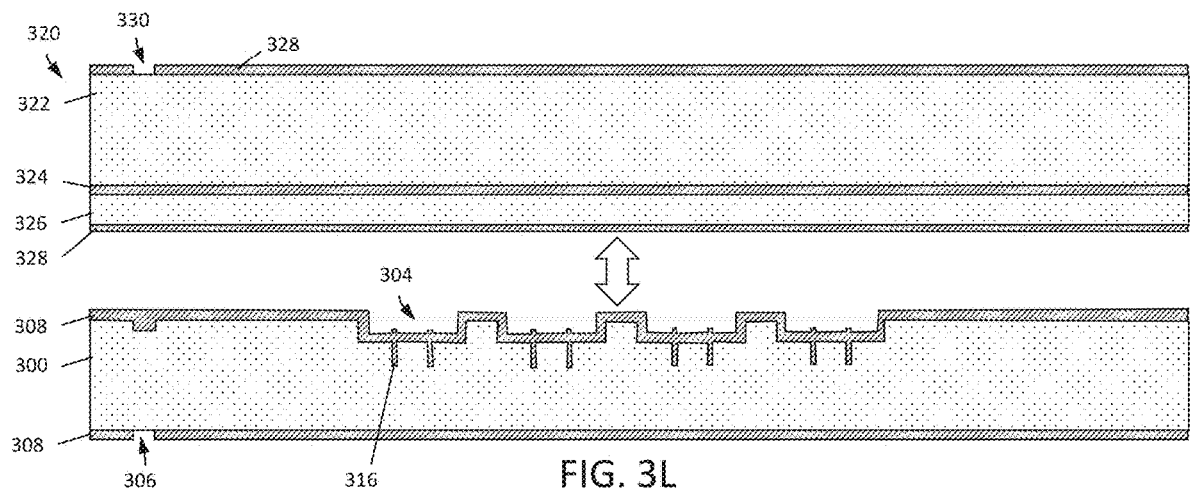
Figure 3M:
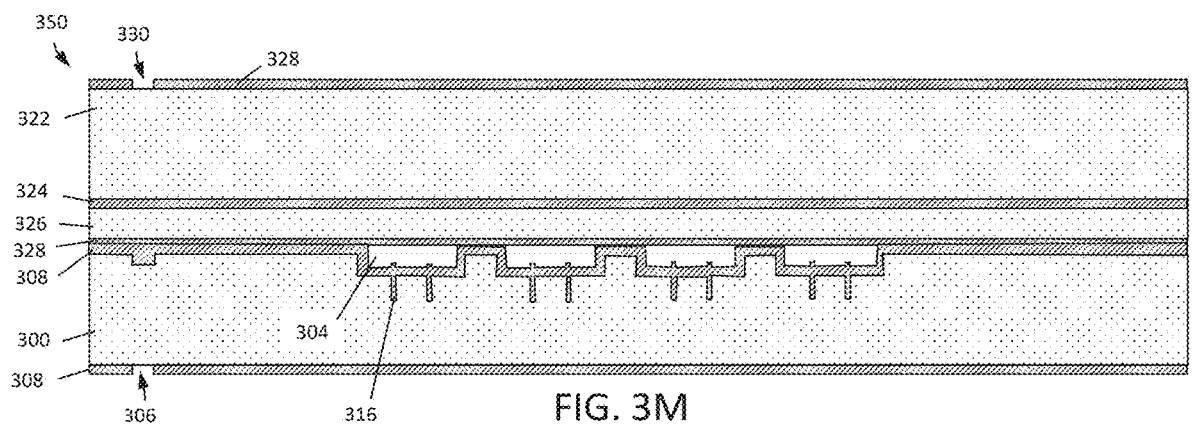
Figure 3N:
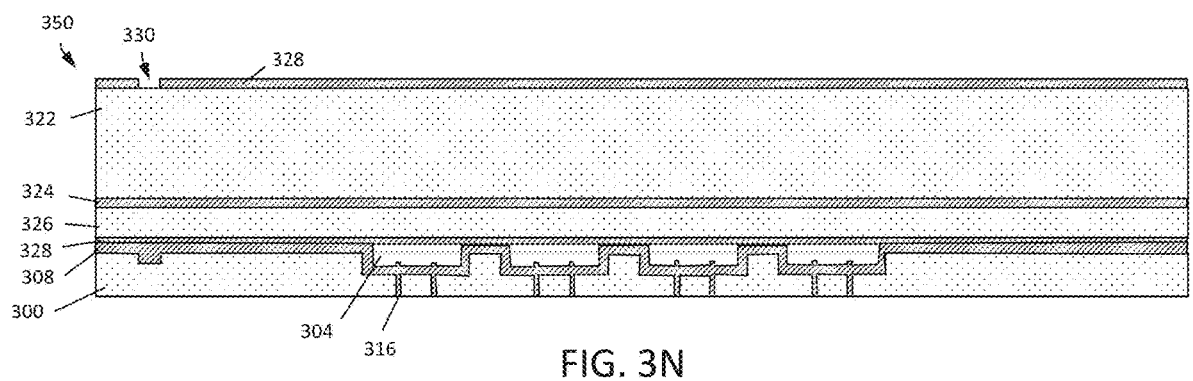
Figure 3O:
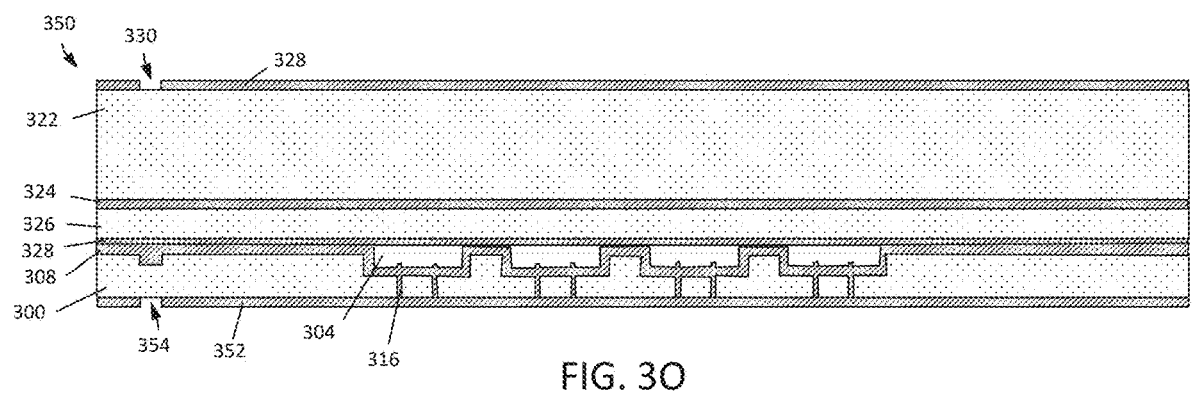
Figure 3P:
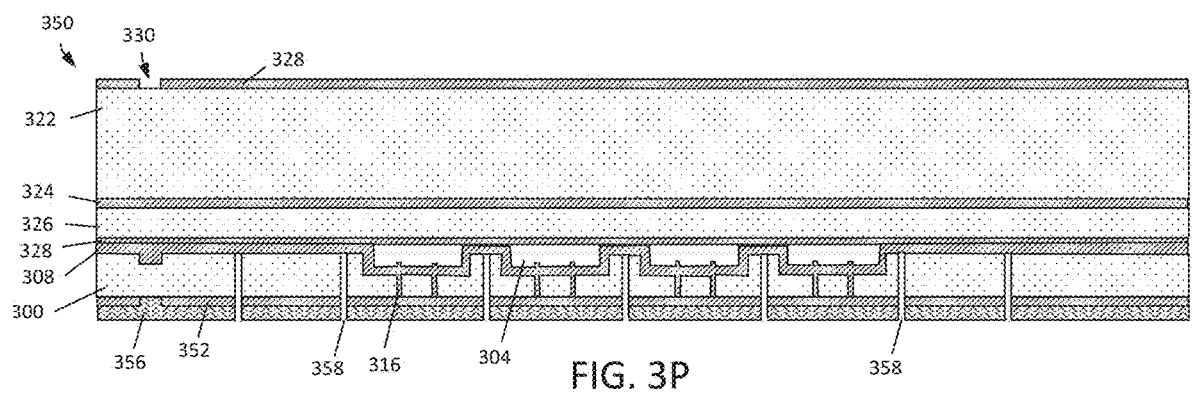
Figure 3Q:
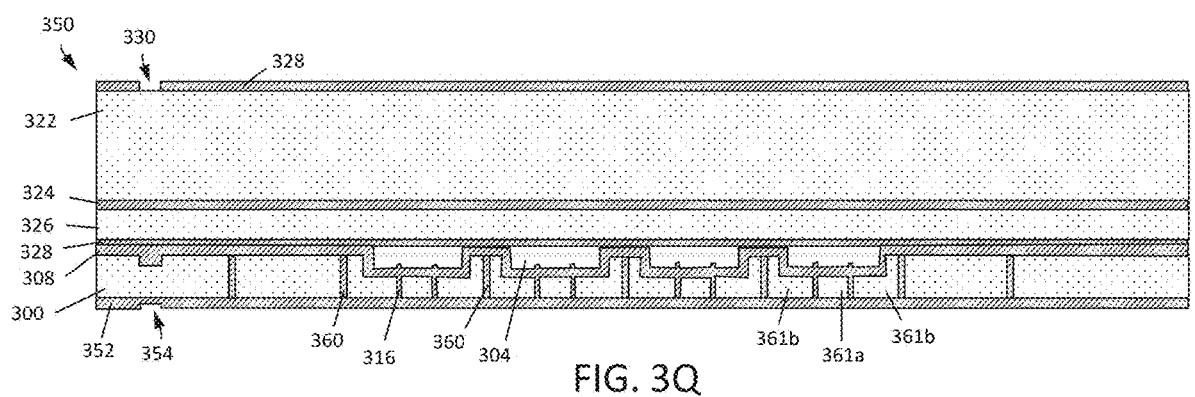
Figure 3R:
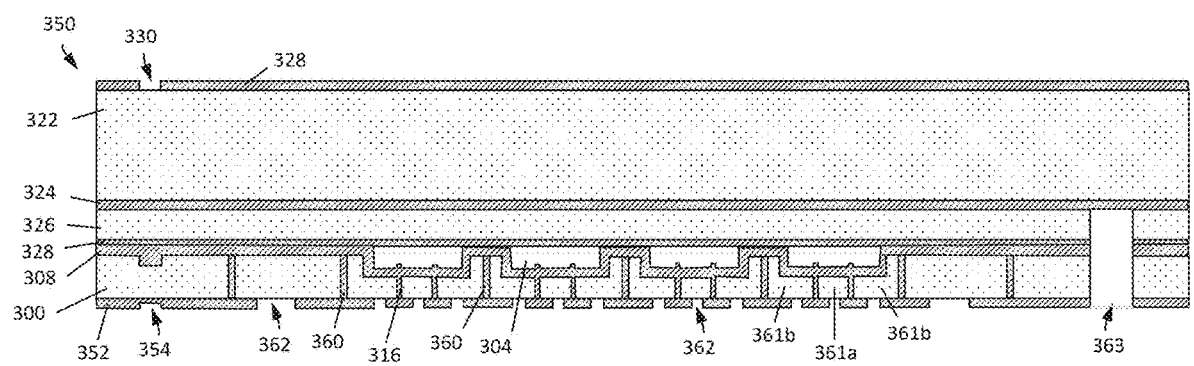
Figure 3S:
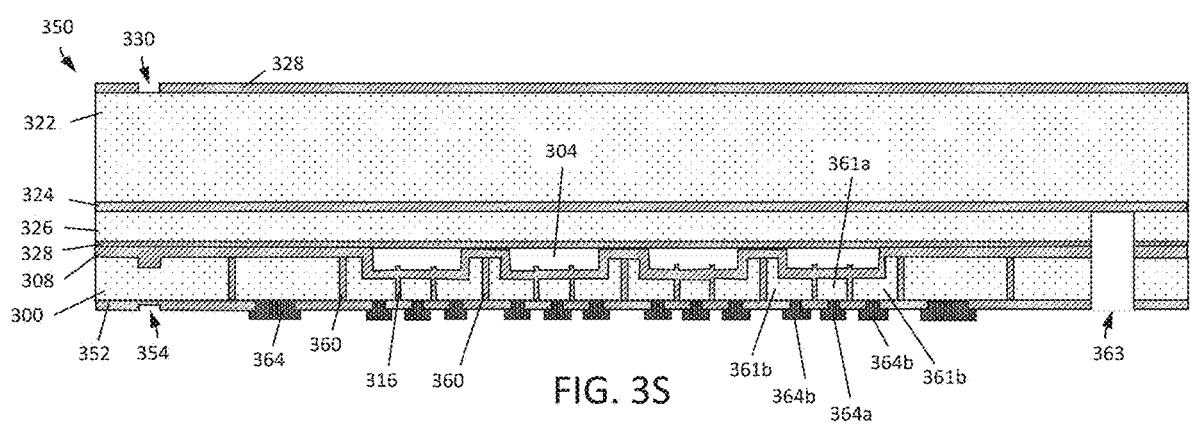

FIGS. 3A-3S illustrate a fabrication sequence for forming the engineered substrate of FIG. 1 and FIG. 2, according to a non-limiting embodiment of the present application. At the outset, it should be appreciated that the exemplary fabrication sequences depicted herein are for illustrative purposes only, and thus the individual features are not necessarily shown to scale, whether in height, width, length, aspect ratio, area or the like.

As shown in FIG. 3A, a first substrate 300 is illustrated. The first substrate 300 may be selected from a suitable semiconductor wafer material, such as single crystal silicon for example, and may be doped in some embodiments to provide desired electrical behavior. Alternative materials include, but are not limited to, polysilicon, amorphous silicon or epitaxial silicon, whether doped or undoped. A doped first substrate 300 may serve as a bottom electrode of an ultrasonic transducer, and in this instance suitable doping may provide desired electrical behavior. In addition, using a doped silicon device layer avoids the need for using TSVs in some embodiments.

In one specific example, the first substrate 300 may be highly a doped p-type substrate having a suitable dopant concentration (e.g., boron) to provide exemplary resistivity ranges of about 10 mΩ·cm-10 Ω·cm, about 10 mΩ·cm-20 mΩ·cm, about 20 mΩ·cm-1 Ω·cm, about 1 Ω·cm-10 Ω·cm, and ranges in between. Alternatively, n-type doping may be used. When doping is used, the doping may be uniform or may be patterned (e.g., by implanting in patterned regions), for example to provide isolated electrodes as described in further detail hereinafter. The first substrate 300 may already be doped upon procurement thereof, or may be doped by ion implantation, as the manner of doping is not limiting in this respect.

As shown in FIG. 3B, a resist layer 602 is used as mask to pattern cavities 304 (i.e., openings that will ultimately define the ultrasonic cavities once sealed) in the first substrate 300. Any suitable number and configuration of cavities 304 may be formed, as the aspects of the application are not limited in this respect. Thus, while only four cavities 304 are illustrated in the non-limiting cross-sectional view of FIG. 3B, it should be appreciated that many more may be formed in some embodiments. For example, an array of cavities 304 may include hundreds of cavities, thousands of cavities, tens of thousands of cavities or more to form an ultrasonic transducer array of a desired size. As also depicted in FIG. 3B, one or more alignment marks 306 may be formed in the resist layer 602 and first substrate 600.

In one embodiment, the cavities 604 may be patterned using a dry silicon etch in which a target etch depth takes into consideration a desired cavity depth plus the thickness of a subsequently formed insulation layer. Thus, by way of example, the cavities 304 may be etched to a depth, d, of about 5000 angstroms (□) (i.e., 0.5 µm), although it will be appreciated that other depths and ranges of depths may be used. In particular, the cavity depth, d, may be selected for desired operation of the ultrasonic transducers ultimately formed (for example) in terms of frequency of operation and/or desired bias voltage. Thus, in some embodiments, d may be approximately 2 µm, approximately 0.5 µm as indicated above, approximately 0.25 µm, between approximately 0.05 µm and approximately 10 µm, between approximately 0.1 µm and approximately 5 µm, between approximately 0.5 µm and approximately 1.5 µm, any depth or range of depths in between, or any other suitable depth.

In addition, the cavities may have a width dimension, w, (e.g., a diameter) of about 200 µm, although other dimensions and ranges of dimensions may be used (e.g., about 50-250 µm). Non-limiting examples of values for w are described further below. The width dimension w may also be used to identify the aperture size of the cavity, and thus the cavities 304 may have apertures of any of the values described herein for w. Further, the cavities 304 may take one of various shapes (as viewed from a top side) to provide a desired membrane shape when the ultrasonic transducers are ultimately formed. For example, the cavities 304 may have a circular contour or a multi-sided contour (e.g., a rectangular contour, a hexagonal contour, an octagonal contour). It will also be appreciated at this point that the specific features of the several Figures herein are not necessarily depicted to scale, but rather are presented for illustrative purposes.

Referring now to FIG. 3C, the resist layer 302 is removed in preparation for insulating layer formation. At this point, one or more etch parameter measurements may be performed (e.g., cavity etch depth), for example to assist in determining a statistical measure(s) of processing capability (e.g., $C_{pk}$). As then shown in FIG. 3D, an insulating layer 308 is formed on outer surfaces of the first substrate 300. The insulating layer 308 may be, for example, a quality oxide of silicon such as $SiO_2$, formed by a thermal oxidation process. Other types of oxide layers and insulating layers in general are also contemplated, however. One exemplary thickness for the insulating layer 308 may be about 2500 □, however other thickness and thickness ranges are also contemplated (e.g., about 500-5000□). The insulating layer 308 may cover both sides of the first substrate 300, and may be formed so as to maintain visibility of the alignment mark 306. This in turn may allow the alignment mark 306 to be transferred from the trench side of the first substrate 300 (e.g., the front side) to the opposite side (e.g., the back side), as shown in FIG. 3E.

In FIG. 3F, a sacrificial hardmask layer 310 is formed over the structure of FIG. 3E. The hardmask layer 310 may be selected from a material such as silicon nitride for example, and have an etch selectivity with respect to oxide material. The sacrificial hardmask layer 310 is then optionally followed by the formation of another resist layer 312, as shown in FIG. 3G.

Referring to FIG. 3H, portions of the cavities 304 are etched through the optional resist layer 312, the sacrificial hardmask layer 310, oxide layer 308 and into the first substrate 300. As described in further detail herein, this etch creates trenches 314 beneath the cavities that ultimately define an intracavity isolation region to electrically separate regions of a bottom electrode of an individual transducer cavity. In an exemplary embodiment, an trench 314 in a given cavity 304 may (when taken from a top view) form a closed contour, such as a circle, oval, square, polygon, etc. The trenches 314 may have an exemplary depth of about 40 μm and an exemplary width of about 1.5 μm, although other dimensions and ranges of dimensions are contemplated so long as the desired intracavity isolation functionality is provided. More specifically, the trench width is adequate to provide electrical isolation, and the width and fill of the isolation trenches may be designed to also allow different voltages to be applied to the different regions separated by these trenches.

FIG. 3I illustrates removal of the resist layer 312 and optional cleaning operation, such as with an SC1 or SC2 clean, an HF dip, a polymer removal, or other suitable cleaning and surface treatment operations, followed by an oxidation fill of the trenches 314 as shown in FIG. 3J. The oxidation fill may, for example, be a thermal oxidation that refills the trenches 314 with about 7500□ of oxide 316. In an alternative embodiment, the oxide 316 may be replaced with undoped polysilicon, a combination of oxide and undoped polysilicon, or other insulating material(s). Notably, the sacrificial hardmask layer 310 may serve to maintain the thickness of the oxide layer 308 on top of the cavities 304 by blocking further oxidation during trench oxidation. There may be some LOCOS growth which may in turn form a slight "bird's beak," or oxide protrusion in the regions immediately adjacent to the openings in the nitride hardmask. This may serve as an advantage in operation of the CMUT by providing regions of maximized receive sensitivity with minimal surface area of membrane touchdown. Then, as shown in FIG. 3K, the sacrificial hardmask layer 310 is removed, such as by a wet etch process with high selectivity to oxide that preserves the thermal oxide surface of oxide layer 308 for subsequent bonding. Other removal processes may also be used however.

Proceeding to FIG. 3L, a second substrate 320 is illustrated in juxtaposition with the first substrate 300. The second substrate 320 may be selected from a suitable semiconductor wafer material, such as silicon-on-insulator (SOI) for example, and may be doped in some embodiments to provide desired electrical behavior. A doped second substrate 320 may include a bulk layer 322, a buried insulator (e.g., oxide) layer 324 (also referred to as a "BOX" layer), and a silicon-on-insulator (SOI) device layer 326 (e.g., silicon) that may serve as a top membrane of an ultrasonic transducer. In one specific example, the SOI silicon device layer 326 of the second substrate 320 may be highly a doped p-type substrate having a suitable dopant concentration (e.g., boron) to provide a resistivity with ranges of about 10 mΩ·cm-10 Ω·cm, about 10 mΩ·cm-20 mΩ·cm, about 20 mΩ·cm-1 Ω·cm, about 1 Ω·cm-10 Ω·cm, and ranges in between. Alternatively, n-type doping may be used. When doping is used, the doping may be uniform or may be patterned (e.g., by implanting in patterned regions. The second substrate 320 may already be doped upon procurement thereof, or may be doped by ion implantation, as the manner of doping is not limiting in this respect. In addition, outer surfaces of the second substrate 320 may oxidized with a quality oxide layer 328 for bonding with the first substrate 300, wherein a thickness of the oxide layer 328 may be determined by a desired gap between the top SOI device silicon layer 326 and the bottom of the cavities 304. Oxide layer 328 may be a thermal silicon oxide, but it should be appreciated that oxides or insulating materials other than thermal oxide may alternatively be used.

As shown in FIG. 3M, the first substrate 600 may be bonded with the second substrate 320 to define an engineered substrate 350. The bonding may be a fusion bonding performed at a low temperature (e.g., a fusion bond below 450° C.), but may also be followed by an anneal at a high temperature (e.g., at greater than 500° C., such as about 1000° C.) to ensure sufficient bond strength. In those embodiments in which the first and/or second substrates 300 and 320 are doped, the anneal may also serve to diffuse and/or activate the doping, meaning that a single anneal may perform multiple functions. In the illustrated embodiment, the bond may be an $SiO_2$—$SiO_2$ bond, although alternatives are possible. For example, in some embodiments the SOI silicon device layer 326 of the second substrate 320 may lack an oxide layer 328, such that the bond between the first and second substrates 300 and 320 may be a Si—$SiO_2$ bond.

Then, as shown in FIG. 3N, the oxide layer 308 and a portion of the substrate 300 may be removed, in any suitable manner. For example, grinding, etching, polishing or any other suitable technique or combination of techniques may be used. As a result, a thickness of the substrate 300 is removed so as to expose the oxide 316 material of the intracavity isolation trenches, leaving a remaining thickness (e.g., less than about 10 μm, about 10 μm-μm, 10 μm-30 μm, 30 μm-40 μm, greater than about 40 μm). It should be noted that the depth of the etched and filled trenches may be varied in anticipation of the desired final thickness of layer 300. For example, if substrate 300 is to be thinned to 30 µm, the trenches 314 may be etched to 40 µm deep to assure full exposure of all trenches and full isolation after thinning substrate 300. FIG. 3O illustrates the formation of another oxide layer 352 on the thinned substrate. The oxide layer 352 may be formed by any suitable method such as, for example, thermal oxidation or by plasma enhanced chemical vapor deposition (PECVD) (e.g., at a thickness range of less than about 1000 angstroms (□), from about 1000 □-1 µm, from about 1000 □-1500 □, from about 1500 □-5000 □, from about 5000 □-1 µm, and greater than about 1-3 µm). Optionally, the alignment mark 330 may be transferred to the oxide layer 352 as alignment mark 354 if desired.

Referring to FIG. 3P, a resist layer 356 may be formed over the oxide layer 352 in order to pattern and define trench openings 358 in substrate 300 that define isolation regions between individual transducer cells and/or elements (i.e., intercavity isolation). Thereafter, the resist layer 356 may be removed, followed by filling the openings with an insulating material 360, such as oxide or an oxide liner with undoped polysilicon fill, for example. In one embodiment, the oxide fill may continue to form an increased amount of oxide on layer 352, as shown in FIG. 3Q. Alternatively, the insulating material 360 may include undoped polysilicon, a combination of oxide and undoped polysilicon, or other insulating material(s). In any case, it will be appreciated that the configuration of the intracavity oxide material 616 and the intercavity oxide material 660 defines electrically isolated and separately electrically addressable regions of a transducer cell. That is, a given cell may have a first bottom electrode portion and a second bottom electrode portion that are electrically isolated from one another, as well as from other transducer cells. Hereinafter, such a first bottom electrode portion and a second bottom electrode portion that are electrically isolated from one another (and therefore separately electrically addressable from one another) are also referred to as an inner electrode 361a and an outer electrode 361b, respectively. One exemplary application of an inner electrode 361a and a separately electrically addressable outer electrode 361b is to have one perform a transmit function of an ultrasound device and the other to perform a receive function of the ultrasound device, thus eliminating the need for a transmit/receive switch in the ultrasound circuitry.

FIG. 3R illustrates the formation of contact openings 362 in layer 352, such as by forming and patterning a resist layer (not shown), in preparation for forming bonding locations for later bonding of the engineered substrate with a CMOS wafer. In addition, a clear out region 363 may be formed through layer 332, substrate 300, oxide layers 308 and 328, and SOI silicon device layer 326. The clear out region 363 may isolate groups of ultrasonic transducers from each other (e.g., separating distinct ultrasonic transducer arrays). For example, in some embodiments the substrate 300 and SOI silicon device layer 326 are retained only in a region corresponding to an ultrasonic transducer array, with the clear out region 363 separating ultrasonic transducer arrays. The clear out region 363 may provide easier access to the CMOS wafer at a periphery of the ultrasonic transducer array, for example allowing for access to bond pads or other electrical connection features, as well as access to scribe lines for alignment during processing or for testing or dicing of completed wafers. The clear out region 363 may be formed in any suitable manner, for example using one or more of grinding, deep reactive ion etching (DRIE) and plasma etches for etching the silicon device layers and oxide layers. In some embodiments, grinding followed by DRIE is used. Alternative manners of forming the clear out region 363 are possible. As mentioned above, features such as the clear out region are not necessarily depicted to scale and are for illustrative purposes only. For example, in the case of the clear out region 363, the aspect ratio may be different than that actually depicted in the figures (e.g., the width dimension may be greater that the depth dimension). It may also be possible to form the clear out region 363 by partial dicing at the end of the line (i.e., cutting through the engineered substrate without cutting into the CMOS wafer, after bonding).

Bonding material 364 may then be formed on the engineered substrate 350 in preparation for bonding the engineered substrate with an electrical substrate such as a CMOS wafer, as shown in FIG. 3S. The type of bonding material 364 may depend on the type of bond to be formed. For example, the bonding material 364 may be a metal suitable for thermocompression bonding, eutectic bonding, or silicide bonding. In some embodiments, the bonding material may be conductive so that electrical signals may be communicated between the engineered substrate and an electrical substrate such as a CMOS wafer. For example, in some embodiments the bonding material 364 may be gold and may be formed by electroplating. In addition, appropriate seed layer metals may be used to prevent unwanted inter-diffusion of materials. In some embodiments, materials and techniques used for wafer level packaging may be applied in the context of bonding the engineered substrate with a CMOS wafer. Thus, for example, stacks of metals selected to provide desirable adhesion, interdiffusion barrier functionality, and high bonding quality may be used, and the bonding material 364 may include such stacks of metals. In one specific example, a seed metal (e.g., one or layers of titanium tungsten (TiW) be deposited over the layer 352 and into the openings 362, followed by metal plating (e.g. Au) and etching of the seed and plated layers to form metal electrode contacts. In addition to TiW/Au, other metallizations may include, but are not limited to, Ti, Ti/TiW/Au, TiW/Ni/Au, TiW/Pd/Au, and TiW/Cu/Ni/Au with Ti or TiW forming the main adhesion layer, TiW, Ni, Pt, Pd, TiN or TaN (optional) functioning as a barrier layer and Au or Cu as the main conductor.

With respect to individual cells or elements, an inner electrode contact 364a may correspond to inner electrode 361a, while an outer electrode contact 364b may correspond to an outer electrode 364b. At this point in the processing, the engineered substrate 350 may be considered to be in condition for bonding to an electrical substrate such as a CMOS wafer to form a monolithically integrated ultrasound-on-a-chip device.

Figure 4A:
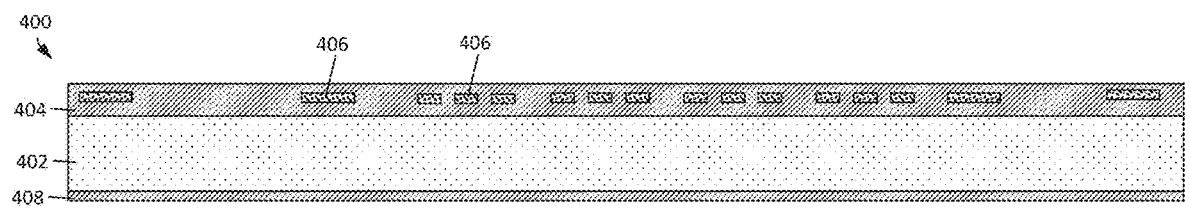
FIGS. 4A-4D illustrate a fabrication sequence for preparing an electrical substrate such as CMOS wafer for bonding with the engineering substrate, according to a non-limiting embodiment of the present application.
Figure 4B:
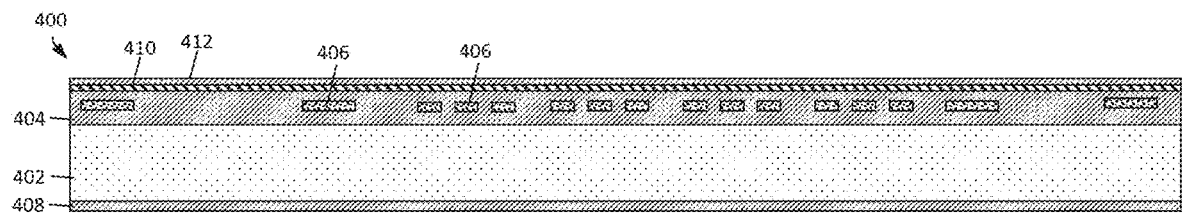

FIGS. 4A-4D illustrate a fabrication sequence for preparing an electrical substrate such as CMOS wafer for bonding with the engineering substrate, according to a non-limiting embodiment of the present application. As shown in FIG. 4A, the CMOS wafer 400 includes a base layer (e.g., a bulk silicon wafer) 402, an insulating layer 404, and metallization 406. An insulating layer 408 may optionally be formed on the backside of the base layer 402. As shown in FIG. 4B, layers 410 and 412 may be formed on the CMOS wafer 400. The layer 410 may be, for example, a nitride layer and may be formed by plasma enhanced chemical vapor deposition (PECVD). The layer 412 may be an oxide layer, for example formed by PECVD of oxide.

Figure 4C:
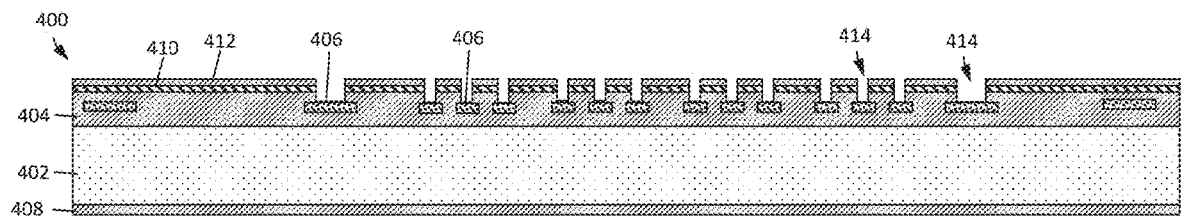
Figure 4D:
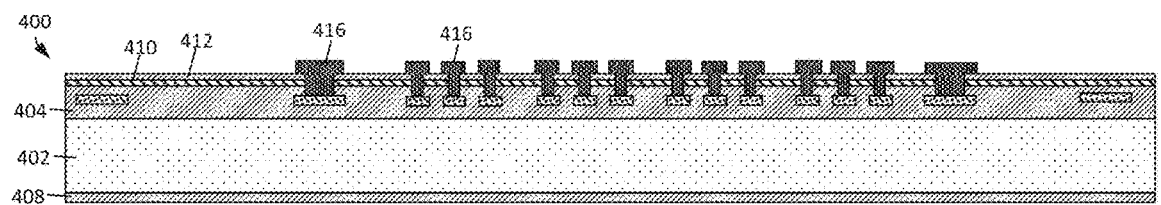

In FIG. 4C, openings 414 may be formed through layers 412, 410 to the metallization 406. Such openings may be made in preparation for forming bonding points. For example, in FIG. 4D, bonding material 416 may be formed on the CMOS wafer 400 (by suitable deposition and patterning) at one or more suitable locations for bonding the engineered substrate 350 with the CMOS wafer 400. The bonding material 416 may be any suitable material for bonding with the bonding material 364 on the engineered substrate. As previously described, in some embodiments a low temperature eutectic bond may be formed, and in such embodiments the bonding material 416 and bonding material 364 may form a eutectic pair. For example, bonding material 364 and bonding material 416 may form an indium-tin (In—Sn) eutectic pair, a gold-tin (Au—Sn) eutectic pair, and aluminum-germanium (Al—Ge) eutectic pair, or a tin-silver-copper (Sn—Ag—Cu) combination. In the case of Sn—Ag—Cu, two of the materials may be formed on the engineered substrate 350 as bonding material 364 with the remaining material formed as bonding material 416.

Figure 5A:
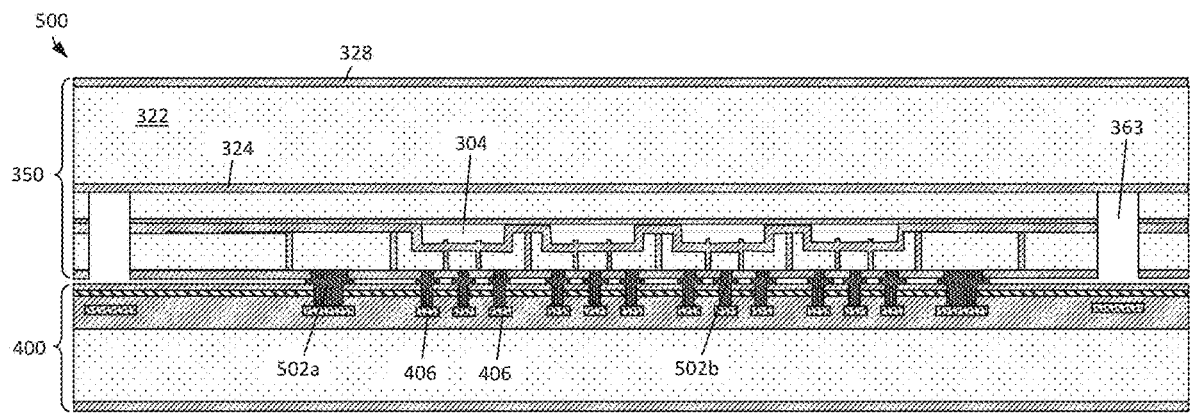
FIGS. 5A-5D illustrate a fabrication sequence for integrating the engineered substrate with the electrical substrate, and encompasses the method of FIG. 1, according to a non-limiting embodiment of the present application.

FIGS. 5A-5D illustrate a fabrication sequence for integrating the engineered substrate with the electrical substrate (CMOS wafer 400), and encompasses the method of FIG. 1, according to a non-limiting embodiment of the present application. As shown in FIG. 5A, the engineered substrate 350 and CMOS wafer 400 may be bonded together, which in some embodiments results in a monolithically integrated structure 500 including sealed cavities 304 disposed vertically above ICs in the CMOS wafer 400 (e.g., metallization 406). As previously described, such bonding may, in some embodiments, involve only the use of low temperature (e.g., below 450° C.) which may prevent damage to metallization layers and other components on the CMOS wafer 400.

In the non-limiting example illustrated, the bond may be a eutectic bond, such that the bonding material 364 and bonding material 416 may in combination form bond points 502a and 502b. As a further non-limiting example, a thermocompression bond may be formed using gold (Au) or other suitable metal as the bonding material. For instance (and as indicated previously), the bonding material 364 may include a seed layer (formed by sputtering or otherwise) of Ti/TiW/Au with plated Au formed thereon, and the bonding material 416 may include a seed layer (formed by sputtering or otherwise) of TiW/Au with plated Ni/Au formed thereon. The layers of titanium may serve as adhesion layers, while the TiW layers may serve as adhesion layers and diffusion barriers. The nickel may serve as a diffusion barrier, while the Au may form the bond. Other bonding materials may alternatively be used.

Figure 5B:
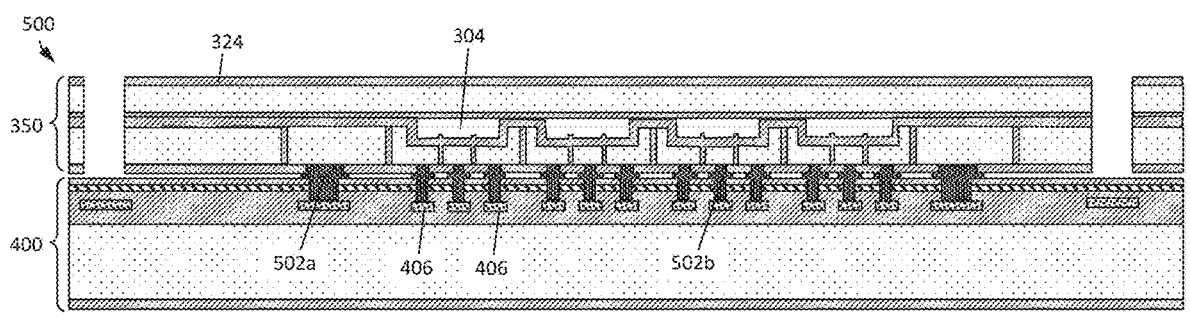
Figure 5C:
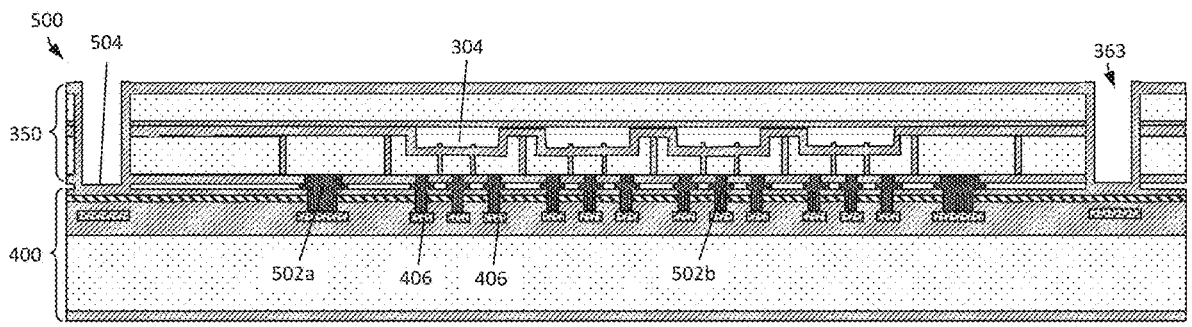
Figure 5D:
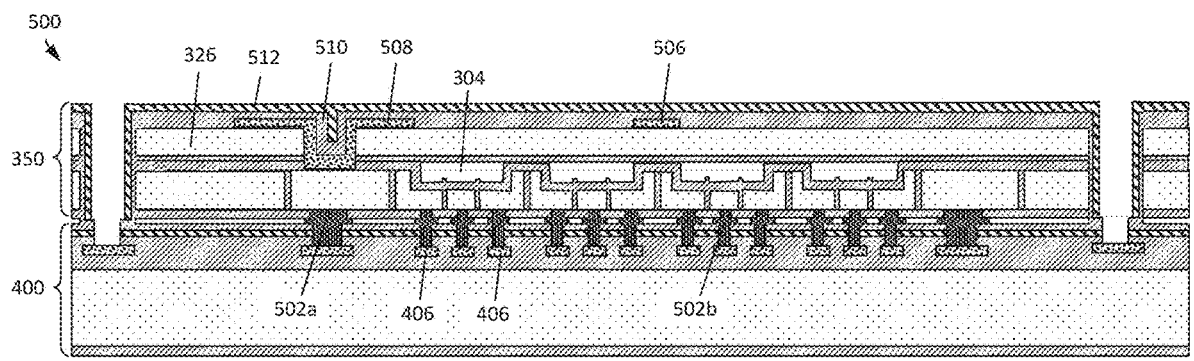

Next, the bulk layer 322 and oxide layer 328 may be removed in any suitable manner as shown in FIG. 5B. For example, grinding and/or etching may be used. The oxide layer 324 may act as an etch stop for removing the bulk layer 322. As shown in FIG. 5C, an additional oxide passivation layer 504 may be formed over the integrated structure 500, which may also form a seal between the engineered substrate 350 and CMOS wafer 400, surrounding the transducer region. Then, as shown in FIG. 5D, additional processing to produce an ultrasound device may include forming first metallic contact(s) 506 and second metallic contact(s) 508 (e.g., aluminum, copper, or other suitable conductive material), where second metallic contact(s) 508 provides a conductive path between the CMOS wafer 400 and the SOI silicon device layer 326 of the engineered substrate 350. As is further illustrated in FIG. 5D, one or more passivation layers (oxide 510, nitride 512 and/or oxide plus nitride) may be also formed over the integrated structure 500.

Various features of the above described fabrication sequences are now noted. For example, it should be appreciated that the fabrication sequences do not involve the use of TSVs, thus making the process less costly and complex than if TSVs were used. The yield of the process may be increased as a result. Moreover, the design rules are less restrictive than would be the case with TSVs. For example, dense, small features may be created whereas TSVs are limited by the aspect ratio, mechanical integrity and processing. That is, TSVs are larger, fewer in number and less dense. In contrast, the present embodiments allow for the fabrication of tens of thousands (or more) of connections per die, which is not possible with TSVs.

Additionally, the process (or processes) does not utilize chemical mechanical polishing (CMP) to form cavities. Similarly, it is noteworthy that the illustrated fabrication sequences do not require any densification anneals (e.g., of PECVD films) for the low temperature bond of the engineered substrate with the CMOS wafer. The use of such anneals may reduce bonding reliability and therefore yield. Densification also introduces variability in dimensional control of the gap and cavity depth, which affect CMUT device performance. Further still, and as previously described, the fabrication of the sealed cavities for the ultrasonic transducers is decoupled from the CMOS thermal budget, thus allowing for use of high temperature processing (e.g., a high temperature anneal) when bonding together the wafers of the engineered substrate.

The process for forming the sealed cavities 304 may also facilitate forming cavities of desired dimensions and spacing. For example, the cavities 304 may have widths w (e.g., see FIGS. 3B and 3C) of approximately 50 μm, between approximately 5 μm and approximately 500 μm, between approximately 20 μm and approximately 200 μm, any width or range of widths in between, or any other suitable widths. In some embodiments, the width w may be selected to maximize the void fraction, being the amount of area consumed by the cavities compared to the amount of area consumed by surrounding structures. The cavities 306 may have depths d (see FIGS. 3B and 3C) of approximately 2 μm, approximately 0.5 am, approximately 0.25 μm, between approximately 0.05 μm and approximately 10 μm, between approximately 0.1 μm and approximately 5 μm, between approximately 0.5 μm and approximately 1.5 μm, any depth or range of depths in between, or any other suitable depths. In some embodiments, the cavities have widths w of approximately 50 μm and depths d of approximately 0.2 μm. In some embodiments, a ratio of the width w to the depth d may be greater than 50, greater than 100, greater than 150, between 30 and 300, or any other suitable ratio. The ratio may be selected to provide desired operation of the transducer membrane, for example operation at a target frequency.

The spacing between cavities 304 may also be made small despite the fact that the amount of space between cavities 304 impacts the bondable area when forming the engineered substrate. That is, the smaller the distances are between the cavities 304 the less bonding surface is available which increases the difficulty of bonding. However, the processes of forming the engineered substrate described herein, including cavity formation in an oxide layer, low temperature fusion bond, and high temperature anneal, make it practical to closely space the cavities 304 while still achieving high bond quality and yield of the engineered substrate. In general, because formation of the engineered substrate is not limited by a thermal budget using the techniques described herein, flexibility is provided in using design rules to minimize the bondable area between cavities 304. For example, spacing between cavities of less than 5 μm, less than 3 µm, or less than 2 µm, among other possibilities, may be achieved using the processes described herein.

It also should be appreciated that the fabrication steps presented herein are not necessarily limited to the order illustrated in the figures, as any other suitable fabrication order may be used. Furthermore, in some embodiments, not all process steps are necessary and one or more process steps may be omitted.

The aspects of the present application may provide one or more benefits, some of which have been previously described. Now described are some non-limiting examples of such benefits. It should be appreciated that not all aspects and embodiments necessarily provide all of the benefits now described. Further, it should be appreciated that aspects of the present application may provide additional benefits to those now described.

Aspects of the present application provide manufacturing processes suitable for formation of monolithically integrated ultrasonic transducers and CMOS structures (e.g., CMOS ICs). Thus, single substrate devices operating as ultrasound devices (e.g., for ultrasound imaging and/or high intensity focused ultrasound (HIFU)) are achieved.

In at least some embodiments, the processes may be reliable (e.g., characterized by high yield and/or high device reliability), scalable to large quantities, and relatively inexpensive to perform, thus contributing to a commercially practical fabrication process for CUTs. The processes may also be repeatable, with tight dimensional tolerances from one transducer element to the next, for all transducers in an array, for all die on a wafer, for all wafers in a lot, and for all wafers and lots run throughout time. Further, the use of complex and costly processing techniques such as the formation of TSVs, the use of precision CMP, the use of densification anneals of low temperature oxide, and bonding of low temperature oxides may be avoided. Moreover, the processes may provide for the fabrication of small ultrasound devices, facilitating the creation of portable ultrasound probes.

In some aspects, the fabrication processes allow for bonding of an engineered substrate with a circuit wafer in a wafer-scale packaging facility, which offer reduced cost compared to performing the bonding in a microfabrication facility. Also, the use of redistribution and fan out or fan in technology may be accommodated, allowing for bonding of circuit wafers with engineered substrates even when the two have differing dimensions, or when dies from the two have differing dimensions. The use of RDL and fan out and/or fan in may also allow for design variation in the engineered substrate without requiring redesign of the circuit wafer or interface layers between the two. Multiple transducer die may be integrated onto one CMOS die or tiled in any combination.

Having thus described several aspects and embodiments of the technology of this application, it is to be appreciated that various alterations, modifications, and improvements will readily occur to those of ordinary skill in the art. Such alterations, modifications, and improvements are intended to be within the spirit and scope of the technology described in the application. For example, those of ordinary skill in the art will readily envision a variety of other means and/or structures for performing the function and/or obtaining the results and/or one or more of the advantages described herein, and each of such variations and/or modifications is deemed to be within the scope of the embodiments described herein. Those skilled in the art will recognize, or be able to ascertain using no more than routine experimentation, many equivalents to the specific embodiments described herein. It is, therefore, to be understood that the foregoing embodiments are presented by way of example only and that, within the scope of the appended claims and equivalents thereto, inventive embodiments may be practiced otherwise than as specifically described. In addition, any combination of two or more features, systems, articles, materials, kits, and/or methods described herein, if such features, systems, articles, materials, kits, and/or methods are not mutually inconsistent, is included within the scope of the present disclosure.

As a non-limiting example, various embodiments have been described as including CMUTs. In alternative embodiments, PMUTs may be used instead of, or in addition to, CMUTs.

Also, as described, some aspects may be embodied as one or more methods. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Elements other than those specifically identified by the "and/or" clause may optionally be present, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

What is claimed is:

1. An apparatus, comprising:
    an ultrasonic transducer substrate having a membrane, a bottom electrode, and a plurality of cavities disposed between the membrane and the bottom electrode, each of the plurality of cavities corresponding to an individual transducer cell;
    wherein portions of the bottom electrode corresponding to each individual transducer cell are electrically isolated from one another; and
    each portion of the bottom electrode corresponding to each individual transducer cell further comprising a first bottom electrode portion and a second bottom electrode portion, the first and second bottom electrode portions electrically isolated from one another;
    first trench isolation regions disposed within the bottom electrode and configured to electrically isolate each individual transducer cell from one another; and
    second trench isolation regions disposed within the bottom electrode and configured to electrically isolate the first and second bottom electrode portions of an individual transducer cell from one another;
    the apparatus further comprising an electrical substrate bonded to the ultrasonic transducer substrate.

2. The apparatus of claim 1, wherein the membrane serves as a top electrode for each of the individual transducer cells.

3. The apparatus of claim 1, wherein the first and second bottom electrode portions of an individual transducer cell are separately electrically addressable from one another.

4. The apparatus of claim 1, wherein the first bottom electrode portion comprises an inner bottom electrode with respect to a diameter of the transducer cell, and the second bottom electrode portion comprises an outer bottom electrode with respect to the diameter of the transducer cell.

5. The apparatus of claim 1, wherein the electrical substrate comprises one of: a CMOS substrate, an analog circuit substrate, an interposer substrate, a printed circuit board (PCB) substrate, and a flexible substrate.

6. The apparatus of claim 5, wherein:
    the electrical substrate comprises a CMOS substrate;
    one of the first bottom electrode portion and the second bottom electrode portion is configured to perform a transmit function of the apparatus; and
    the other of the first bottom electrode portion and the second bottom electrode portion is configured to perform a receive function of the apparatus.

* * * * *